US012708709B2

(12) United States Patent
Lee et al.

(10) Patent No.: US 12,708,709 B2
(45) Date of Patent: Aug. 18, 2026

(54) ADAPTATION OF AUTOMATIC INSULIN DELIVERY (AID) FOR USERS WITH BASAL TO BOLUS MISMATCH

(71) Applicant: Insulet Corporation, Acton, MA (US)

(72) Inventors: Joon Bok Lee, Acton, MA (US); Yibin Zheng, Hartland, WI (US); Jason O'Connor, Acton, MA (US)

(73) Assignee: INSULET CORPORATION, Acton, MA (US)

( * ) Notice: Subject to any disclaimer, the term of this patent is extended or adjusted under 35 U.S.C. 154(b) by 1143 days.

(21) Appl. No.: 17/684,652

(22) Filed: Mar. 2, 2022

(65) Prior Publication Data

US 2022/0280721 A1 Sep. 8, 2022

Related U.S. Application Data

(60) Provisional application No. 63/155,555, filed on Mar. 2, 2021.

(51) Int. Cl.
*A61M 5/172* (2006.01)
*G16H 20/17* (2018.01)

(52) U.S. Cl.
CPC .......... *A61M 5/1723* (2013.01); *G16H 20/17* (2018.01); *A61M 2230/20* (2013.01)

(58) Field of Classification Search
CPC .............. G16H 20/17; A61M 2230/20; A61M 2230/201; A61M 5/14532; A61M 5/1723; A61M 5/1726
See application file for complete search history.

(56) References Cited

U.S. PATENT DOCUMENTS

| | | | |
|---|---|---|---|
| 303,013 | A | 8/1884 | Horton |
| 2,797,149 | A | 6/1957 | Skeggs |
| 3,631,847 | A | 1/1972 | Hobbs |
| 3,634,039 | A | 1/1972 | Brondy |
| 3,812,843 | A | 5/1974 | Wootten et al. |
| 3,841,328 | A | 10/1974 | Jensen |
| 3,963,380 | A | 6/1976 | Thomas, Jr. et al. |

(Continued)

FOREIGN PATENT DOCUMENTS

| | | |
|---|---|---|
| AU | 2015200834 A1 | 3/2015 |
| AU | 2015301146 A1 | 3/2017 |

(Continued)

OTHER PUBLICATIONS

US 5,954,699 A, 09/1999, Jost et al. (withdrawn)

(Continued)

*Primary Examiner* — Wesley G Harris
*Assistant Examiner* — Charles W Nichols
(74) *Attorney, Agent, or Firm* — Goodwin Procter LLP

(57) ABSTRACT

Exemplary embodiments provide more customized basal insulin amounts for users to better regulate blood glucose (BG) concentration levels. The exemplary embodiments do not statically assume that the daily basal amount for each user is 50% of TDI. Instead, actual TDI data may be gathered for each user and may be used to adjust the TDI value for that user to an updated value. In addition, the ratio of basal to TDI may be adjusted for the user based on the actual ratio determined from data gathered over one or more days. As a result, better BG concentration level control may be realized.

20 Claims, 10 Drawing Sheets

(56) References Cited

U.S. PATENT DOCUMENTS 4,055,175 A 10/1977 Clemens et al.
4,146,029 A 3/1979 Ellinwood, Jr.
4,151,845 A 5/1979 Clemens
4,245,634 A 1/1981 Albisser et al.
4,368,980 A 1/1983 Aldred et al.
4,373,527 A 2/1983 Fischell
4,403,984 A 9/1983 Ash et al.
4,464,170 A 8/1984 Clemens et al.
4,469,481 A 9/1984 Kobayashi
4,475,901 A 10/1984 Kraegen et al.
4,526,568 A 7/1985 Clemens et al.
4,526,569 A 7/1985 Bernardi
4,529,401 A 7/1985 Leslie et al.
4,559,033 A 12/1985 Stephen et al.
4,559,037 A 12/1985 Franetzki et al.
4,573,968 A 3/1986 Parker
4,624,661 A 11/1986 Arimond
4,633,878 A 1/1987 Bombardieri
4,657,529 A 4/1987 Prince et al.
4,685,903 A 8/1987 Cable et al.
4,731,726 A 3/1988 Allen, III
4,743,243 A 5/1988 Vaillancourt
4,755,173 A 7/1988 Konopka et al.
4,781,688 A 11/1988 Thoma et al.
4,781,693 A 11/1988 Martinez et al.
4,808,161 A 2/1989 Kamen
4,854,170 A 8/1989 Brimhall et al.
4,886,499 A 12/1989 Cirelli et al.
4,900,292 A 2/1990 Berry et al.
4,919,596 A 4/1990 Slate et al.
4,925,444 A 5/1990 Orkin et al.
4,940,527 A 7/1990 Kazlauskas et al.
4,975,581 A 12/1990 Robinson et al.
4,976,720 A 12/1990 Machold et al.
4,981,140 A 1/1991 Wyatt
4,994,047 A 2/1991 Walker et al.
5,007,286 A 4/1991 Malcolm et al.
5,097,834 A 3/1992 Skrabal
5,102,406 A 4/1992 Arnold
5,109,850 A 5/1992 Blanco et al.
5,125,415 A 6/1992 Bell
5,134,079 A 7/1992 Cusack et al.
5,153,827 A 10/1992 Coutre et al.
5,165,406 A 11/1992 Wong
5,176,662 A 1/1993 Bartholomew et al.
5,178,609 A 1/1993 Ishikawa
5,207,642 A 5/1993 Orkin et al.
5,232,439 A 8/1993 Campbell et al.
5,237,993 A 8/1993 Skrabal
5,244,463 A 9/1993 Cordner, Jr. et al.
5,257,980 A 11/1993 Van Antwerp et al.
5,273,517 A 12/1993 Barone et al.
5,281,808 A 1/1994 Kunkel
5,299,571 A 4/1994 Mastrototaro
5,308,982 A 5/1994 Ivaldi et al.
5,342,298 A 8/1994 Michaels et al.
5,377,674 A 1/1995 Kuestner
5,380,665 A 1/1995 Cusack et al.
5,385,539 A 1/1995 Maynard
5,389,078 A 2/1995 Zalesky
5,411,889 A 5/1995 Hoots et al.
5,421,812 A 6/1995 Langley et al.
5,468,727 A 11/1995 Phillips et al.
5,505,709 A 4/1996 Funderburk et al.
5,505,828 A 4/1996 Wong et al.
5,507,288 A 4/1996 Bocker et al.
5,533,389 A 7/1996 Kamen et al.
5,558,640 A 9/1996 Pfeiler et al.
5,569,186 A 10/1996 Lord et al.
5,584,813 A 12/1996 Livingston et al.
5,609,572 A 3/1997 Lang
5,665,065 A 9/1997 Colman et al.
5,678,539 A 10/1997 Schubert et al.
5,685,844 A 11/1997 Marttila
5,685,859 A 11/1997 Kornerup
5,693,018 A 12/1997 Kriesel et al.
5,697,899 A 12/1997 Hillman et al.
5,700,695 A 12/1997 Yassinzadeh et al.
5,703,364 A 12/1997 Rosenthal
5,714,123 A 2/1998 Sohrab
5,716,343 A 2/1998 Kriesel et al.
5,722,397 A 3/1998 Eppstein
5,741,228 A 4/1998 Lambrecht et al.
5,746,217 A 5/1998 Erickson et al.
5,755,682 A 5/1998 Knudson et al.
5,758,643 A 6/1998 Wong et al.
5,800,405 A 9/1998 McPhee
5,800,420 A 9/1998 Gross et al.
5,801,057 A 9/1998 Smart et al.
5,804,048 A 9/1998 Wong et al.
5,817,007 A 10/1998 Fodgaard et al.
5,820,622 A 10/1998 Gross et al.
5,823,951 A 10/1998 Messerschmidt
5,840,020 A 11/1998 Heinonen et al.
5,848,991 A 12/1998 Gross et al.
5,851,197 A 12/1998 Marano et al.
5,858,005 A 1/1999 Kriesel
5,865,806 A 2/1999 Howell
5,871,470 A 2/1999 McWha
5,879,310 A 3/1999 Sopp et al.
5,902,253 A 5/1999 Pfeiffer et al.
5,931,814 A 8/1999 Alex et al.
5,932,175 A 8/1999 Knute et al.
5,935,099 A 8/1999 Peterson et al.
5,947,911 A 9/1999 Wong et al.
5,971,941 A 10/1999 Simons et al.
5,993,423 A 11/1999 Choi
5,997,501 A 12/1999 Gross et al.
6,017,318 A 1/2000 Gauthier et al.
6,024,539 A 2/2000 Blomquist
6,032,059 A 2/2000 Henning et al.
6,036,924 A 3/2000 Simons et al.
6,040,578 A 3/2000 Malin et al.
6,049,727 A 4/2000 Crothall
6,050,978 A 4/2000 Orr et al.
6,058,934 A 5/2000 Sullivan
6,066,103 A 5/2000 Duchon et al.
6,071,292 A 6/2000 Makower et al.
6,072,180 A 6/2000 Kramer et al.
6,077,055 A 6/2000 Vilks
6,090,092 A 7/2000 Fowles et al.
6,101,406 A 8/2000 Hacker et al.
6,102,872 A 8/2000 Doneen et al.
6,115,673 A 9/2000 Malin et al.
6,123,827 A 9/2000 Wong et al.
6,124,134 A 9/2000 Stark
6,126,637 A 10/2000 Kriesel et al.
6,128,519 A 10/2000 Say
6,142,939 A 11/2000 Eppstein et al.
6,143,164 A 11/2000 Heller et al.
6,157,041 A 12/2000 Thomas et al.
6,161,028 A 12/2000 Braig et al.
6,162,639 A 12/2000 Douglas
6,196,046 B1 3/2001 Braig et al.
6,200,287 B1 3/2001 Keller et al.
6,200,338 B1 3/2001 Solomon et al.
6,214,629 B1 4/2001 Freitag et al.
6,226,082 B1 5/2001 Roe
6,244,776 B1 6/2001 Wiley
6,261,065 B1 7/2001 Nayak et al.
6,262,798 B1 7/2001 Shepherd et al.
6,270,455 B1 8/2001 Brown
6,271,045 B1 8/2001 Douglas et al.
6,280,381 B1 8/2001 Malin et al.
6,285,448 B1 9/2001 Kuenstner
6,309,370 B1 10/2001 Haim et al.
6,312,888 B1 11/2001 Wong et al.
6,334,851 B1 1/2002 Hayes et al.
6,375,627 B1 4/2002 Mauze et al.
6,379,301 B1 4/2002 Worthington et al.
6,402,689 B1 6/2002 Scarantino et al.
6,470,279 B1 10/2002 Samsoondar
6,475,196 B1 11/2002 Vachon
6,477,901 B1 11/2002 Tadigadapa et al.

(56) References Cited

U.S. PATENT DOCUMENTS 6,484,044 B1 11/2002 Lilienfeld-Toal
6,491,656 B1 12/2002 Morris
6,512,937 B2 1/2003 Blank et al.
6,525,509 B1 2/2003 Petersson et al.
6,528,809 B1 3/2003 Thomas et al.
6,540,672 B1 4/2003 Simonsen et al.
6,544,212 B2 4/2003 Galley et al.
6,546,268 B1 4/2003 Ishikawa et al.
6,546,269 B1 4/2003 Kurnik
6,553,841 B1 4/2003 Blouch
6,554,798 B1 4/2003 Mann et al.
6,556,850 B1 4/2003 Braig et al.
6,558,351 B1 5/2003 Steil et al.
6,560,471 B1 5/2003 Heller et al.
6,561,978 B1 5/2003 Conn et al.
6,562,001 B2 5/2003 Lebel et al.
6,562,014 B2 5/2003 Lin et al.
6,569,125 B2 5/2003 Jepson et al.
6,572,542 B1 6/2003 Houben et al.
6,572,545 B2 6/2003 Knobbe et al.
6,574,490 B2 6/2003 Abbink et al.
6,575,905 B2 6/2003 Knobbe et al.
6,580,934 B1 6/2003 Braig et al.
6,618,603 B2 9/2003 Varalli et al.
6,633,772 B2 10/2003 Ford et al.
6,645,142 B2 11/2003 Braig et al.
6,653,091 B1 11/2003 Dunn et al.
6,662,030 B2 12/2003 Khalil et al.
6,669,663 B1 12/2003 Thompson
6,678,542 B2 1/2004 Braig et al.
6,699,221 B2 3/2004 Vaillancourt
6,718,189 B2 4/2004 Rohrscheib et al.
6,721,582 B2 4/2004 Trepagnier et al.
6,728,560 B2 4/2004 Kollias et al.
6,740,059 B2 5/2004 Flaherty
6,740,072 B2 5/2004 Starkweather et al.
6,751,490 B2 6/2004 Esenaliev et al.
6,758,835 B2 7/2004 Close et al.
6,780,156 B2 8/2004 Haueter et al.
6,810,290 B2 10/2004 Lebel et al.
6,837,858 B2 1/2005 Cunningham et al.
6,837,988 B2 1/2005 Eong et al.
6,846,288 B2 1/2005 Nagar et al.
6,862,534 B2 3/2005 Sterling et al.
6,865,408 B1 3/2005 Abbink et al.
6,890,291 B2 5/2005 Robinson et al.
6,936,029 B2 8/2005 Mann et al.
6,949,081 B1 9/2005 Chance
6,958,809 B2 10/2005 Sterling et al.
6,989,891 B2 1/2006 Braig et al.
6,990,366 B2 1/2006 Say et al.
7,008,404 B2 3/2006 Nakajima
7,009,180 B2 3/2006 Sterling et al.
7,016,713 B2 3/2006 Gardner et al.
7,018,360 B2 3/2006 Flaherty et al.
7,025,743 B2 4/2006 Mann et al.
7,025,744 B2 4/2006 Utterberg et al.
7,027,848 B2 4/2006 Robinson et al.
7,043,288 B2 5/2006 Davis, III et al.
7,060,059 B2 6/2006 Keith et al.
7,061,593 B2 6/2006 Braig et al.
7,096,124 B2 8/2006 Sterling et al.
7,115,205 B2 10/2006 Robinson et al.
7,128,727 B2 10/2006 Flaherty et al.
7,139,593 B2 11/2006 Kavak et al.
7,139,598 B2 11/2006 Hull et al.
7,144,384 B2 12/2006 Gorman et al.
7,171,252 B1 1/2007 Scarantino et al.
7,190,988 B2 3/2007 Say et al.
7,204,823 B2 4/2007 Estes et al.
7,248,912 B2 7/2007 Gough et al.
7,267,665 B2 9/2007 Steil et al.
7,271,912 B2 9/2007 Sterling et al.
7,278,983 B2 10/2007 Ireland et al.
7,291,107 B2 11/2007 Hellwig et al.
7,291,497 B2 11/2007 Holmes et al.
7,303,549 B2 12/2007 Flaherty et al.
7,303,622 B2 12/2007 Loch et al.
7,303,922 B2 12/2007 Jeng et al.
7,354,420 B2 4/2008 Steil et al.
7,388,202 B2 6/2008 Sterling et al.
7,402,153 B2 7/2008 Steil et al.
7,404,796 B2 7/2008 Ginsberg
7,429,255 B2 9/2008 Thompson
7,460,130 B2 12/2008 Salganicoff
7,481,787 B2 1/2009 Gable et al.
7,491,187 B2 2/2009 Van Den Berghe et al.
7,500,949 B2 3/2009 Gottlieb et al.
7,509,156 B2 3/2009 Flanders
7,547,281 B2 6/2009 Hayes et al.
7,569,030 B2 8/2009 Lebel et al.
7,608,042 B2 10/2009 Goldberger et al.
7,651,845 B2 1/2010 Doyle, III et al.
7,680,529 B2 3/2010 Kroll
7,734,323 B2 6/2010 Blomquist et al.
7,766,829 B2 8/2010 Sloan et al.
7,785,258 B2 8/2010 Braig et al.
7,806,854 B2 10/2010 Damiano et al.
7,806,886 B2 10/2010 Kanderian, Jr. et al.
7,918,825 B2 4/2011 OConnor et al.
7,946,985 B2 5/2011 Mastrototaro et al.
7,972,296 B2 7/2011 Braig et al.
8,221,345 B2 7/2012 Blomquist
8,251,907 B2 8/2012 Sterling et al.
8,449,524 B2 5/2013 Braig et al.
8,452,359 B2 5/2013 Rebec et al.
8,454,576 B2 6/2013 Mastrototaro et al.
8,467,980 B2 6/2013 Campbell et al.
8,478,557 B2 7/2013 Hayter et al.
8,547,239 B2 10/2013 Peatfield et al.
8,597,274 B2 12/2013 Sloan et al.
8,622,988 B2 1/2014 Hayter
8,810,394 B2 8/2014 Kalpin
9,061,097 B2 6/2015 Holt et al.
9,171,343 B1 10/2015 Fischell et al.
9,233,204 B2 1/2016 Booth et al.
9,486,571 B2 11/2016 Rosinko
9,579,456 B2 2/2017 Budiman et al.
9,743,224 B2 8/2017 San Vicente et al.
9,907,515 B2 3/2018 Doyle, III et al.
9,980,140 B1 5/2018 Spencer et al.
9,984,773 B2 5/2018 Gondhalekar et al.
10,248,839 B2 4/2019 Levy et al.
10,335,464 B1 7/2019 Michelich et al.
10,583,250 B2 3/2020 Mazlish et al.
10,737,024 B2 8/2020 Schmid
10,987,468 B2 4/2021 Mazlish et al.
11,197,964 B2 12/2021 Sjolund et al.
11,260,169 B2 3/2022 Estes
2001/0021803 A1 9/2001 Blank et al.
2001/0034023 A1 10/2001 Stanton, Jr. et al.
2001/0034502 A1 10/2001 Moberg et al.
2001/0051377 A1 12/2001 Hammer et al.
2001/0053895 A1 12/2001 Vaillancourt
2002/0010401 A1 1/2002 Bushmakin et al.
2002/0010423 A1 1/2002 Gross et al.
2002/0016568 A1 2/2002 Lebel et al.
2002/0040208 A1 4/2002 Flaherty et al.
2002/0123740 A1 9/2002 Flaherty et al.
2002/0128543 A1 9/2002 Leonhardt
2002/0147423 A1 10/2002 Burbank et al.
2002/0155425 A1 10/2002 Han et al.
2002/0161288 A1 10/2002 Shin et al.
2003/0023148 A1 1/2003 Lorenz et al.
2003/0050621 A1 3/2003 Lebel et al.
2003/0060692 A1 3/2003 Ruchti et al.
2003/0086074 A1 5/2003 Braig et al.
2003/0086075 A1 5/2003 Braig et al.
2003/0090649 A1 5/2003 Sterling et al.
2003/0100040 A1 5/2003 Bonnecaze et al.
2003/0130616 A1 7/2003 Steil et al.
2003/0135388 A1 7/2003 Martucci et al.
2003/0144582 A1 7/2003 Cohen et al.
2003/0163097 A1 8/2003 Fleury et al.

(56) References Cited

U.S. PATENT DOCUMENTS

2003/0195404 A1 10/2003 Knobbe et al.
2003/0208113 A1 11/2003 Mault et al.
2003/0208154 A1 11/2003 Close et al.
2003/0212379 A1 11/2003 Bylund et al.
2003/0216627 A1 11/2003 Lorenz et al.
2003/0220605 A1 11/2003 Bowman, Jr. et al.
2004/0010207 A1 1/2004 Flaherty et al.
2004/0034295 A1 2/2004 Salganicoff
2004/0045879 A1 3/2004 Shults et al.
2004/0051368 A1 3/2004 Caputo et al.
2004/0064259 A1 4/2004 Haaland et al.
2004/0097796 A1 5/2004 Berman et al.
2004/0116847 A1 6/2004 Wall
2004/0122353 A1 6/2004 Shahmirian et al.
2004/0133166 A1 7/2004 Moberg et al.
2004/0147034 A1 7/2004 Gore et al.
2004/0171983 A1 9/2004 Sparks et al.
2004/0203357 A1 10/2004 Nassimi
2004/0204868 A1 10/2004 Maynard et al.
2004/0215492 A1 10/2004 Choi
2004/0220517 A1 11/2004 Starkweather et al.
2004/0241736 A1 12/2004 Hendee et al.
2004/0249308 A1 12/2004 Forssell
2005/0003470 A1 1/2005 Nelson et al.
2005/0020980 A1 1/2005 Inoue et al.
2005/0022274 A1 1/2005 Campbell et al.
2005/0033148 A1 2/2005 Haueter et al.
2005/0049179 A1 3/2005 Davidson et al.
2005/0065464 A1 3/2005 Talbot et al.
2005/0065465 A1 3/2005 Lebel et al.
2005/0075624 A1 4/2005 Miesel
2005/0105095 A1 5/2005 Pesach et al.
2005/0137573 A1 6/2005 McLaughlin
2005/0171503 A1 8/2005 Van Den Berghe et al.
2005/0182306 A1 8/2005 Sloan
2005/0192494 A1 9/2005 Ginsberg
2005/0192557 A1 9/2005 Brauker et al.
2005/0197621 A1 9/2005 Poulsen et al.
2005/0203360 A1 9/2005 Brauker et al.
2005/0203461 A1 9/2005 Flaherty et al.
2005/0238507 A1 10/2005 Dilanni et al.
2005/0261660 A1 11/2005 Choi
2005/0272640 A1 12/2005 Doyle, III et al.
2005/0277912 A1 12/2005 John
2006/0009727 A1 1/2006 OMahony et al.
2006/0079809 A1 4/2006 Goldberger et al.
2006/0100494 A1 5/2006 Kroll
2006/0134323 A1 6/2006 OBrien
2006/0167350 A1 7/2006 Monfre et al.
2006/0173406 A1 8/2006 Hayes et al.
2006/0189925 A1 8/2006 Gable et al.
2006/0189926 A1 8/2006 Hall et al.
2006/0197015 A1 9/2006 Sterling et al.
2006/0200070 A1 9/2006 Callicoat et al.
2006/0204535 A1 9/2006 Johnson
2006/0229531 A1 10/2006 Goldberger et al.
2006/0253085 A1 11/2006 Geismar et al.
2006/0264895 A1 11/2006 Flanders
2006/0270983 A1 11/2006 Lord et al.
2006/0276771 A1 12/2006 Galley et al.
2006/0282290 A1 12/2006 Flaherty et al.
2007/0016127 A1 1/2007 Staib et al.
2007/0060796 A1 3/2007 Kim
2007/0060869 A1 3/2007 Tolle et al.
2007/0060872 A1 3/2007 Hall et al.
2007/0083160 A1 4/2007 Hall et al.
2007/0106135 A1 5/2007 Sloan et al.
2007/0116601 A1 5/2007 Patton
2007/0118405 A1 5/2007 Campbell et al.
2007/0129690 A1 6/2007 Rosenblatt et al.
2007/0142720 A1 6/2007 Ridder et al.
2007/0173761 A1 7/2007 Kanderian et al.
2007/0173974 A1 7/2007 Lin et al.
2007/0179352 A1 8/2007 Randlov et al.
2007/0191716 A1 8/2007 Goldberger et al.
2007/0197163 A1 8/2007 Robertson
2007/0225675 A1 9/2007 Robinson et al.
2007/0244381 A1 10/2007 Robinson et al.
2007/0249007 A1 10/2007 Rosero
2007/0264707 A1 11/2007 Liederman et al.
2007/0282269 A1 12/2007 Carter et al.
2007/0287985 A1 12/2007 Estes et al.
2007/0293843 A1 12/2007 Ireland et al.
2008/0033272 A1 2/2008 Gough et al.
2008/0051764 A1 2/2008 Dent et al.
2008/0058625 A1 3/2008 McGarraugh et al.
2008/0065050 A1 3/2008 Sparks et al.
2008/0071157 A1 3/2008 McGarraugh et al.
2008/0071158 A1 3/2008 McGarraugh et al.
2008/0078400 A1 4/2008 Martens et al.
2008/0097289 A1 4/2008 Steil et al.
2008/0132880 A1 6/2008 Buchman
2008/0161664 A1 7/2008 Mastrototaro et al.
2008/0172026 A1 7/2008 Blomquist
2008/0177165 A1 7/2008 Blomquist et al.
2008/0188796 A1 8/2008 Steil et al.
2008/0200838 A1 8/2008 Goldberger et al.
2008/0206067 A1 8/2008 De Corral et al.
2008/0208113 A1 8/2008 Damiano et al.
2008/0214919 A1 9/2008 Harmon et al.
2008/0228056 A1 9/2008 Blomquist et al.
2008/0249386 A1 10/2008 Besterman et al.
2008/0269585 A1 10/2008 Ginsberg
2008/0269714 A1 10/2008 Mastrototaro et al.
2008/0269723 A1 10/2008 Mastrototaro et al.
2008/0287906 A1 11/2008 Burkholz et al.
2009/0006061 A1 1/2009 Thukral et al.
2009/0018406 A1 1/2009 Yodfat et al.
2009/0030398 A1 1/2009 Yodfat et al.
2009/0036753 A1 2/2009 King
2009/0043240 A1 2/2009 Robinson et al.
2009/0054753 A1 2/2009 Robinson et al.
2009/0069743 A1 3/2009 Krishnamoorthy et al.
2009/0069745 A1 3/2009 Estes et al.
2009/0069787 A1 3/2009 Estes et al.
2009/0099521 A1 4/2009 Gravesen et al.
2009/0105573 A1 4/2009 Malecha
2009/0131861 A1 5/2009 Braig et al.
2009/0156922 A1 6/2009 Goldberger et al.
2009/0156924 A1 6/2009 Shariati et al.
2009/0163781 A1 6/2009 Say et al.
2009/0198350 A1 8/2009 Thiele
2009/0221890 A1 9/2009 Saffer et al.
2009/0228214 A1 9/2009 Say et al.
2009/0318791 A1 12/2009 Kaastrup
2009/0326343 A1 12/2009 Gable et al.
2010/0057042 A1 3/2010 Hayter
2010/0114026 A1 5/2010 Karratt et al.
2010/0121170 A1 5/2010 Rule
2010/0137784 A1 6/2010 Cefai et al.
2010/0152658 A1 6/2010 Hanson et al.
2010/0174228 A1 7/2010 Buckingham et al.
2010/0211003 A1 8/2010 Sundar et al.
2010/0228110 A1 9/2010 Tsoukalis
2010/0262117 A1 10/2010 Magni et al.
2010/0262434 A1 10/2010 Shaya
2010/0295686 A1 11/2010 Sloan et al.
2010/0298765 A1 11/2010 Budiman et al.
2011/0021584 A1 1/2011 Berggren et al.
2011/0028817 A1 2/2011 Jin et al.
2011/0054390 A1 3/2011 Searle et al.
2011/0054399 A1 3/2011 Chong et al.
2011/0124996 A1 5/2011 Reinke et al.
2011/0144586 A1 6/2011 Michaud et al.
2011/0160652 A1 6/2011 Yodfat et al.
2011/0178472 A1 7/2011 Cabiri
2011/0190694 A1 8/2011 Lanier, Jr. et al.
2011/0202005 A1 8/2011 Yodfat et al.
2011/0218495 A1 9/2011 Remde
2011/0230833 A1 9/2011 Landman et al.
2011/0251509 A1 10/2011 Beyhan et al.
2011/0313680 A1 12/2011 Doyle et al.
2011/0316562 A1 12/2011 Cefai et al.
2012/0003935 A1 1/2012 Lydon et al.

(56) References Cited

U.S. PATENT DOCUMENTS

2012/0010594 A1 1/2012 Holt et al.
2012/0030393 A1 2/2012 Ganesh et al.
2012/0053556 A1 3/2012 Lee
2012/0078067 A1 3/2012 Kovatchev et al.
2012/0078161 A1 3/2012 Masterson et al.
2012/0078181 A1 3/2012 Smith et al.
2012/0101451 A1 4/2012 Boit et al.
2012/0123234 A1 5/2012 Atlas et al.
2012/0136336 A1 5/2012 Mastrototaro et al.
2012/0190955 A1 7/2012 Rao et al.
2012/0203085 A1 8/2012 Rebec
2012/0203178 A1 8/2012 Tverskoy
2012/0215087 A1 8/2012 Cobelli et al.
2012/0225134 A1 9/2012 Komorowski
2012/0226259 A1 9/2012 Yodfat et al.
2012/0232520 A1 9/2012 Sloan et al.
2012/0238851 A1 9/2012 Kamen et al.
2012/0271655 A1 10/2012 Knobel et al.
2012/0277668 A1 11/2012 Chawla
2012/0282111 A1 11/2012 Nip et al.
2012/0295550 A1 11/2012 Wilson et al.
2013/0030358 A1 1/2013 Yodfat et al.
2013/0158503 A1 6/2013 Kanderian, Jr. et al.
2013/0178791 A1 7/2013 Javitt
2013/0231642 A1 9/2013 Doyle et al.
2013/0253472 A1 9/2013 Cabiri
2013/0261406 A1 10/2013 Rebec et al.
2013/0296823 A1 11/2013 Melker et al.
2013/0317753 A1 11/2013 Kamen et al.
2013/0338576 A1 12/2013 OConnor et al.
2014/0005633 A1 1/2014 Finan
2014/0066886 A1 3/2014 Roy et al.
2014/0066889 A1 3/2014 Grosman et al.
2014/0074033 A1 3/2014 Sonderegger et al.
2014/0121635 A1 5/2014 Hayter
2014/0128839 A1 5/2014 Dilanni et al.
2014/0135880 A1 5/2014 Baumgartner et al.
2014/0146202 A1 5/2014 Boss et al.
2014/0180203 A1 6/2014 Budiman et al.
2014/0180240 A1 6/2014 Finan et al.
2014/0200426 A1 7/2014 Taub et al.
2014/0200559 A1 7/2014 Doyle et al.
2014/0230021 A1 8/2014 Birthwhistle et al.
2014/0276554 A1 9/2014 Finan et al.
2014/0276556 A1 9/2014 Saint et al.
2014/0278123 A1 9/2014 Prodhom et al.
2014/0309615 A1 10/2014 Mazlish
2014/0316379 A1 10/2014 Sonderegger et al.
2014/0325065 A1 10/2014 Birtwhistle et al.
2015/0018633 A1 1/2015 Kovachev et al.
2015/0025329 A1 1/2015 Amarasingham et al.
2015/0025495 A1 1/2015 Peyser
2015/0120317 A1 4/2015 Mayou et al.
2015/0134265 A1 5/2015 Kohlbrecher et al.
2015/0165119 A1 6/2015 Palerm et al.
2015/0173674 A1 6/2015 Hayes et al.
2015/0213217 A1 7/2015 Amarasingham et al.
2015/0217052 A1 8/2015 Keenan et al.
2015/0217053 A1 8/2015 Booth et al.
2015/0265767 A1 9/2015 Vazquez et al.
2015/0306314 A1 10/2015 Doyle et al.
2015/0351671 A1 12/2015 Vanslyke et al.
2015/0366945 A1 12/2015 Greene
2016/0015891 A1 1/2016 Papiorek
2016/0038673 A1 2/2016 Morales
2016/0038689 A1 2/2016 Lee et al.
2016/0051749 A1 2/2016 Istoc
2016/0082187 A1 3/2016 Schaible et al.
2016/0089494 A1 3/2016 Guerrini
2016/0175520 A1 6/2016 Palerm et al.
2016/0228641 A1 8/2016 Gescheit et al.
2016/0243318 A1 8/2016 Despa et al.
2016/0256087 A1 9/2016 Doyle et al.
2016/0287512 A1 10/2016 Cooper et al.
2016/0302054 A1 10/2016 Kimura et al.
2016/0331310 A1 11/2016 Kovatchev
2016/0354543 A1 12/2016 Cinar et al.
2017/0049386 A1 2/2017 Abraham et al.
2017/0143899 A1 5/2017 Gondhalekar et al.
2017/0143900 A1 5/2017 Rioux et al.
2017/0156682 A1 6/2017 Doyle et al.
2017/0173261 A1 6/2017 OConnor et al.
2017/0189625 A1 7/2017 Cirillo et al.
2017/0281877 A1 10/2017 Marlin et al.
2017/0296746 A1 10/2017 Chen et al.
2017/0311903 A1 11/2017 Davis et al.
2017/0332952 A1 11/2017 Desborough et al.
2017/0348482 A1 12/2017 Duke et al.
2018/0036495 A1 2/2018 Searle et al.
2018/0040255 A1 2/2018 Freeman et al.
2018/0075200 A1 3/2018 Davis et al.
2018/0075201 A1 3/2018 Davis et al.
2018/0075202 A1 3/2018 Davis et al.
2018/0092576 A1 4/2018 O'Connor et al.
2018/0126073 A1 5/2018 Wu et al.
2018/0169334 A1 6/2018 Grosman et al.
2018/0200434 A1* 7/2018 Mazlish ................ G16H 40/60
2018/0200438 A1 7/2018 Mazlish et al.
2018/0200441 A1 7/2018 Desborough et al.
2018/0204636 A1 7/2018 Edwards et al.
2018/0277253 A1 9/2018 Gondhalekar et al.
2018/0289891 A1 10/2018 Finan et al.
2018/0296757 A1 10/2018 Finan et al.
2018/0342317 A1 11/2018 Skirble et al.
2018/0369479 A1 12/2018 Hayter et al.
2019/0076600 A1 3/2019 Grosman et al.
2019/0240403 A1 8/2019 Palerm et al.
2019/0290844 A1 9/2019 Monirabbasi et al.
2019/0336683 A1 11/2019 O'Connor et al.
2019/0336684 A1 11/2019 O'Connor et al.
2019/0348157 A1 11/2019 Booth et al.
2019/0348164 A1 11/2019 Bengtsson et al.
2020/0046268 A1 2/2020 Patek et al.
2020/0101222 A1 4/2020 Lintereur et al.
2020/0101223 A1 4/2020 Intereur et al.
2020/0101225 A1 4/2020 O'Connor et al.
2020/0219625 A1 7/2020 Kahlbaugh
2020/0342974 A1* 10/2020 Chen ..................... G16H 20/17
2021/0050085 A1 2/2021 Hayter et al.
2021/0098105 A1 4/2021 Lee et al.
2022/0023536 A1 1/2022 Graham et al.

FOREIGN PATENT DOCUMENTS

CN 1297140 A 5/2001
DE 19756872 A1 7/1999
EP 0341049 A2 11/1989
EP 0496305 A2 7/1992
EP 0549341 A1 6/1993
EP 1491144 A1 12/2004
EP 0801578 B1 7/2006
EP 2139382 A1 1/2010
EP 2397181 A1 12/2011
EP 2666520 A1 11/2013
EP 2695573 A2 2/2014
EP 2830499 A1 2/2015
EP 2943149 A1 11/2015
EP 3177344 A1 6/2017
EP 3314548 A1 5/2018
EP 1571582 B1 4/2019
EP 2897071 B1 5/2019
EP 3607985 A1 2/2020
GB 2443261 A 4/2008
JP 51125993 A 11/1976
JP 02131777 A 5/1990
JP 2004283378 A 10/2007
JP 2011518634 A 6/2011
JP 2017525451 A 9/2017
JP 2018153569 A 10/2018
JP 2019525276 A 9/2019
JP 2021507395 A 2/2021
TW 200740148 A 10/2007
TW M452390 U 5/2013
WO 9800193 A1 1/1998

(56) References Cited

FOREIGN PATENT DOCUMENTS

| | | | |
|---|---|---|---|
| WO | 9956803 | A1 | 11/1999 |
| WO | 0030705 | A1 | 6/2000 |
| WO | 200032258 | A1 | 6/2000 |
| WO | 0172354 | A2 | 10/2001 |
| WO | 2002015954 | A1 | 2/2002 |
| WO | 2002043866 | A2 | 6/2002 |
| WO | 2002082990 | A1 | 10/2002 |
| WO | 2003016882 | A1 | 2/2003 |
| WO | 2003039362 | A1 | 5/2003 |
| WO | 2003045233 | A1 | 6/2003 |
| WO | 2004043250 | A1 | 5/2004 |
| WO | 2005110601 | A1 | 5/2004 |
| WO | 2004092715 | A1 | 10/2004 |
| WO | 2005051170 | A2 | 6/2005 |
| WO | 2005082436 | A1 | 9/2005 |
| WO | 2005113036 | A1 | 12/2005 |
| WO | 2006053007 | A2 | 5/2006 |
| WO | 2007064835 | A2 | 6/2007 |
| WO | 2007078937 | A1 | 7/2007 |
| WO | 2008024810 | A2 | 2/2008 |
| WO | 2008029403 | A1 | 3/2008 |
| WO | 2008133702 | A1 | 11/2008 |
| WO | 2009045462 | A1 | 4/2009 |
| WO | 2009049252 | A1 | 4/2009 |
| WO | 2009066287 | A3 | 5/2009 |
| WO | 2009066288 | A1 | 5/2009 |
| WO | 2009098648 | A2 | 8/2009 |
| WO | 2009134380 | A2 | 11/2009 |
| WO | 2010053702 | A1 | 5/2010 |
| WO | 2010132077 | A1 | 11/2010 |
| WO | 2010138848 | A1 | 12/2010 |
| WO | 2010147659 | A2 | 12/2010 |
| WO | 2011095483 | A1 | 8/2011 |
| WO | 2012045667 | A2 | 4/2012 |
| WO | 2012108959 | A1 | 8/2012 |
| WO | 2012134588 | A1 | 10/2012 |
| WO | 2012177353 | A1 | 12/2012 |
| WO | 2012178134 | A2 | 12/2012 |
| WO | 2013078200 | A1 | 5/2013 |
| WO | 2013134486 | A2 | 9/2013 |
| WO | 20130149186 | A1 | 10/2013 |
| WO | 2013177565 | A1 | 11/2013 |
| WO | 2013182321 | A1 | 12/2013 |
| WO | 2014109898 | A1 | 7/2014 |
| WO | 2014110538 | A1 | 7/2014 |
| WO | 2014194183 | A2 | 12/2014 |
| WO | 2015056259 | A1 | 4/2015 |
| WO | 2015061493 | A1 | 4/2015 |
| WO | 2015073211 | A1 | 5/2015 |
| WO | 2015081337 | A2 | 6/2015 |
| WO | 2015187366 | A1 | 12/2015 |
| WO | 2016004088 | A1 | 1/2016 |
| WO | 2016022650 | A1 | 2/2016 |
| WO | 2016041873 | A1 | 3/2016 |
| WO | 2016089702 | A1 | 6/2016 |
| WO | 2016141082 | A1 | 9/2016 |
| WO | 2016161254 | A1 | 10/2016 |
| WO | 2017004278 | A1 | 1/2017 |
| WO | 2017091624 | A1 | 6/2017 |
| WO | 2017105600 | A1 | 6/2017 |
| WO | 2017184988 | A1 | 10/2017 |
| WO | 2017205816 | A1 | 11/2017 |
| WO | 2018009614 | A1 | 1/2018 |
| WO | 2018067748 | A1 | 4/2018 |
| WO | 2018120104 | A1 | 7/2018 |
| WO | 2018136799 | A1 | 7/2018 |
| WO | 2018204568 | A1 | 11/2018 |
| WO | 2019077482 | A1 | 4/2019 |
| WO | 2019094440 | A1 | 5/2019 |
| WO | 2019213493 | A1 | 11/2019 |
| WO | 2019246381 | A1 | 12/2019 |
| WO | 2020081393 | A1 | 4/2020 |
| WO | 2021011738 | A1 | 1/2021 |

OTHER PUBLICATIONS

Fox, Ian G.; Machine Learning for Physiological Time Series: Representing and Controlling Blood Glucose for Diabetes Management; University of Michigan. ProQuest Dissertations Publishing, 2020. 28240142. (Year: 2020).

Anonymous: “Artificial pancreas—Wikipedia”, Mar. 13, 2018 (Mar. 13, 2018), XP055603712, Retrieved from the Internet: URL: https://en.wikipedia.org/wiki/Artificial_pancreas [retrieved on Jul. 9, 2019] section “Medical Equipment” and the figure labeled “The medical equipment approach to an artifical pancreas”.

Kaveh et al., “Blood Glucose Regulation via Double Loop Higher Order Sliding Mode Control and Multiple Sampling Rate.” Paper presented at the proceedings of the 17th IFAC World Congress, Seoul, Korea (Jul. 2008).

Dassau et al., “Real-Time Hypoglycemia Prediction Suite Using Contineous Glucose Monitoring,” Diabetes Care, vol. 33, No. 6, 1249-1254 (2010).

International Search Report and Written Opinion for International Patent Application No. PCT/US17/53262, mailed on Dec. 13, 2017, 8 pages.

Van Heusden et al., “Control-Relevant Models for Glucose Control using A Priori Patient Characteristics”, IEEE Transactions on Biomedical Engineering, vol. 59, No. 7, (Jul. 1, 2012) pp. 1839-1849.

Doyle III et al., “Run-to-Run Control Strategy for Diabetes Management.” Paper presented at 23rd Annual International Conference of the IEEE Engineering in Medicine and Biology Society, Istanbul, Turkey. (Oct. 2001).

Bequette, B.W., and Desemone, J., “Intelligent Dosing Systems”: Need for Design and Analysis Based on Control Theory, Diabetes Technology and Therapeutics 9(6): 868-873 (2004).

Parker et al., “A Model-Based Agorithm for Blood Gucose Control in Type 1 Diabetic Patients.” IEEE Transactions on Biomedical Engineering, 46 (2) 148-147 (1999).

International Search Report and Written Opinion for International Patent Application No. PCT/US2017/015601, mailed May 16, 2017, 12 pages.

International Search Report and Written Opinion for the International Patent Application No. PCT/US2018/018901, mailed on Aug. 6, 2018, 12 pages.

International Search Report and Written Opinion for International Patent Application No. PCT/US2018/052467, mailed Jan. 4, 2019, 13 pages.

“How to Create a QR Code that Deep Links to Your Mobile App”, Pure Oxygen Labs, web<https://pureoxygenlabs.com/how-to-create-a-qr-codes-that-deep-link-to-your-mobile-app/> Year:2017.

“Read NFC Tags with an iPHone App on iOS 11”, GoToTags, Sep. 11, 2017, web <https://gototags.com/blog/read-nfc-tags-with-an-iphone-app-on-ios-11/> (Year:2017).

International Search Report and Written Opinion for International Patent Application No. PCT/US2016/063350, mailed on Mar. 27, 2017, 9 pages.

Extended Search Report mailed Aug. 13, 2018, issued in European Patent Application No. 16753053.4, 9 pages.

International Search Report and Written Opinion for International Patent Application No. PCT/US16/18452, mailed on Apr. 29, 2015, 9 pages.

International Preliminary Report on Patentability mailed Aug. 31, 2017, issued in PCT Patent Application No. PCT/US2016/018452, 7 pages.

International Search Report and Written Opinion for International Patent Application No. PCT/US2019/055862, mailed on Mar. 11, 2020.

International Search Report and Written Opinion for Application No. PCT/US2019/030562, Sep. 25, 2019, 19 bages.

International Search Report and Written Opinion for the International Patent Application No. PCT/US2020/052125, mailed Aug. 12, 2020, 15 pages.

International Search Report and Written Opinion for the International Patent Application No. PCT/US2020/050332, mailed Sep. 12, 2020, 12 pages.

(56) References Cited

OTHER PUBLICATIONS

European Patent Office, "Notification of Transmittal of the ISR and the Written Opinion of the International Searching Authority, or the Declaration," in PCT Application No. PCT/GB2015/050248, Jun. 23, 2015, 12 pages.
International Search Report and Written Opinion for the International Patent Application No. PCT/US2021/012246, mailed Apr. 13, 2021, 15 pages.
International Search Report and Written Opinion for the International Patent Application No. PCT/US2021/013639, mailed Apr. 28, 2021, 14 pages.
International Search Report and Written Opinion for the International Patent Application No. PCT/US2020/063326, mailed May 3, 2021, 17 pages.
European Search Report for the European Patent Application No. 21168591, mailed Oct. 13, 2021, 4 pages.
International Search Report and Written Opinion for the International Patent Application No. PCT/US2021/041954, mailed Oct. 25, 2021, 13 pages.
International Search Report and Written Opinion for the International Patent Application No. PCT/US2021/022694, mailed Jun. 25, 2021, 13 pages.
International Search Report and Written Opinion for the International Patent Application No. PCT/US2021/017664, mailed May 26, 2021, 16 pages.
International Search Report and Written Opinion for the International Patent Application No. PCT/US2022/012896, mailed Apr. 22, 2022, 15 pages.
International Search Report and Written Opinion for the International Patent Application No. PCT/US2022/013470, mailed May 6, 2022, 14 pages.
International Search Report and Written Opinion for the International Patent Application No. PCT/US2022/013473, mailed May 6, 2022, 13 pages.
International Search Report and Written Opinion for the International Patent Application No. PCT/US2022/019079, mailed Jun. 2, 2022, 14 pages.
International Search Report and Written Opinion for the International Patent Application No. PCT/US2022/018453, mailed Jun. 2, 2022, 13 pages.
International Search Report and Written Opinion for the International Patent Application No. PCT/US22/018700, mailed Jun. 7, 2022, 13 pages.
International Search Report and Written Opinion for the International Patent Application No. PCT/US22/019080, mailed Jun. 7, 2022, 14 pages.
International Search Report and Written Opinion for the International Patent Application No. PCT/US22/019664, mailed Jun. 7, 2022, 14 pages.
International Search Report and Written Opinion for International Patent Application No. PCT/US2021/051027, mailed on Jan. 7, 2022, 16 pages.
International Search Report and Written Opinion for International Patent Application No. PCT/US2021/052372, mailed Jan. 26, 2022, 15 pages.
International Search Report and Written Opinion for the International Patent Application No. PCT/US2021/046607, mailed Jan. 31, 2022, 20 pages.
International Search Report and Written Opinion for the International Patent Application No. PCT/US2021/055745, mailed Feb. 14, 2022, 13 pages.
International Search Report and Written Opinion for the International Patent Application No. PCT/US21/060618, mailed Mar. 21, 2022, 15 pages.
Herrero Pau et al: "Enhancing automatic closed-loop glucose control in type 1 diabetes with an adaptive meal bolus calculator -in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.
Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].
Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/ master/lib/determine-basal/determine-basal.js [retrieved on Jun. 6, 2022] line 116-line 118, line 439-line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].
Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/Issues/2473 [retrieved on Jun. 6, 2022].
International Search Report and Written Opinion for the International Patent Application No. PCT/US2021/052855, mailed Dec. 22, 2021, 11 pages.
International Search Report and Written Opinion for the International Patent Application No. PCT/US2021/047771, mailed Dec. 22, 2021, 11 pages.
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.
Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.
Unger, Jeff, et al., "Glucose Control in the Hospitalized Patient," Emerg. Med 36(9):12-18 (2004).
"Glucommander FAQ" downloaded from https://adaendo.com/GlucommanderFAQ.html on Mar. 16, 2009.
Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.
Letters to the Editor regarding "Glucose Control in Critically Ill Patients," N Engl J Med 361: 1, Jul. 2, 2009.
"Medtronic is Leading a Highly Attractive Growth Market," Jun. 2, 2009.
Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.
Davidson, Paul C., et al. "Pumpmaster and Glucommander," presented at the MiniMed Symposium, Atlanta GA, Dec. 13, 2003.
Kanji S., et al. "Reliability of point-of-care testing for glucose measurement in critically ill adults," Critical Care Med, vol. 33, No. 12, pp. 2778-2785, 2005.
Krinsley James S., "Severe hypoglycemia in critically ill patients: Risk factors and outcomes," Critical Care Med, vol. 35, No. 10, pp. 1-6, 2007.
International Search Report and Written Opinion for the International Patent Application No. PCT/US2021/016283, mailed Jun. 2, 2021, 15 pages.

(56) References Cited

OTHER PUBLICATIONS

Farkas et al. "Single-Versus Triple-Lumen Central Catheter-Related Sepsis: A Prospective Randomized Study in a Critically Ill Population" The American Journal of Medicine, Sep. 1992, vol. 93, p. 277-282.
Davidson, Paul C., et al., A computer-directed intravenous insulin system shown to be safe, simple, and effective in 120,618 h of operation, Diabetes Care, vol. 28, No. 10, Oct. 2005, pp. 2418-2423.
R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.
Gorke, A "Microbial Contamination Of Haemodialysis Catheter Connections" Journal of Renal Care, European Dialysis & Transplant Nurses Association.
Lovich et al. "Central venous catheter infusions: A laboratory model shows large differences in drug delivery dynamics related to catheter dead volume" Critical Care Med 2007 vol. 35, No. 12.
Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.
Schlegel et al., "Multilumen Central Venous Catheters Increase Risk for Catheter-Related Bloodstream Infection: Prospective Surveillance Study" Infection 2008; 36: 322-327.
Wilson, George S., et al., Progress toward the Development of an Implantable Sensor for Glucose, Clin. Chem., vol. 38, No. 9, 1992, pp. 1613-1617.
Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.
International Search Report and Written Opinion, International Application No. PCT/US2010/033794 mailed Jul. 16, 2010 (OPTIS.247VPC).
International Search Report and Written Opinion in PCT/US2008/079641 (Optis.203VPC) dated Feb. 25, 2009.
Berger, "Measurement of Analytes in Human Serum and Whole Blood Samples by Near-Infrared Raman Spectroscopy," Ph.D. Thesis, Massachusetts Institute of Technology, Chapter 4, pp. 50-73, 1998.
Berger, "An Enhanced Algorithm for Linear Multivariate Calibration," Analytical Chemistry, vol. 70, No. 3, pp. 623-627, Feb. 1, 1998.
Billman et al., "Clinical Performance of an In line Ex-Vivo Point of Care Monitor: A Multicenter Study," Clinical Chemistry 48: 11, pp. 2030-2043, 2002.
Widness et al., "Clinical Performance on an In-Line Point-of-Care Monitor in Neonates"; Pediatrics, vol. 106, No. 3, pp. 497-504, Sep. 2000.
Finkielman et al., "Agreement Between Bedside Blood and Plasma Glucose Measurement in the ICU Setting"; retrieved from http://www.chestjournal.org; CHEST/127/5/May 2005.
Glucon Critical Care Blood Glucose Monitor; Glucon; retrieved from http://www.glucon.com.
Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.
Vonach et al., "Application of Mid-Infrared Transmission Spectrometry to the Direct Determination of Glucose in Whole Blood," Applied Spectroscopy, vol. 52, No. 6, 1998, pp. 820-822.
Muniyappa et al., "Current Approaches for assessing insulin sensitivity and resistance in vivo: advantages, imitations, and appropriate usage," AJP-Endocrinol Metab, vol. 294, E15-E26, first published Oct. 23, 2007.
International Preliminary Report on Patentability for the International Patent Application No. PCT/US2019/053603, mailed Apr. 8, 2021, 9 pages.
International Search Report and Written Opinion for the International Patent Application No. PCT/US2019/053603, mailed Jan. 7, 2020, 16 pages.
Dassau et al., "Detection of a meal using continuous glucose monitoring: Implications for an artificial [beta]-cell." Diabetes Care, American Diabetes Association, Alexandria, VA, US, 31(2):295-300 (2008).
Cameron et al., "Probabilistic Evolving Meal Detection and Estimation of Meal Total Glucose Appearance Author Affiliations", J Diabetes Sci and Tech,Vol., Diabetes Technology Society ;(5):1022-1030 (2009).
Lee et al., "A closed-loop artificial pancreas based on model predictive control: Human-friendly identification and automatic meal disturbance rejection", Biomedical Signal Processing and Control, Elsevier, Amsterdam, NL, 4(4):1746-8094 (2009).
Anonymous: "Fuzzy control system", Wikipedia, Jan. 10, 2020. URL: https://en.wikipedia.org/w/index.php?title=Fuzzy_control_system&oldid=935091190.
An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.
International Search Report and Written Opinion for the InternationalPatent Application No. PCT/US2021/017441, mailed May 25, 2021, 12 pages.
Mirko Messori et al: "Individualized model predictive control for the artificial pancreas: In silico evaluation of closed-loop glucose control", IEEE Control Systems, vol. 38, No. 1, Feb. 1, 2018, pp. 86-104.
International Search Report and Written Opinion for the International Patent Application No. PCT/US2021/017662, mailed May 26, 2021, 14 pages.
Anonymous: "Reservoir Best Practice and Top Tips" Feb. 7, 2016, URL: https://www.medtronic-diabetes.co.uk/blog/reservoir-best-practice-and-top-tips, p. 1.
Gildon Bradford: "InPen Smart Insulin Pen System: Product Review and User Experience" Diabetes Spectrum, vol. 31, No. 4, Nov. 15, 2018, pp. 354-358.
International Search Report and Written Opinion for the International Patent Application No. PCT/US2021/016050, mailed May 27, 2021, 16 pages.
International Search Report and Written Opinion for the International Patent Application No. PCT/US2020/065226, mailed May 31, 2021, 18 pages.
International Search Report and Written Opinion for the International Patent Application No. PCT/US2021/017659, mailed May 31, 2021, 13 pages.
Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.
Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.
Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.
Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.
E. Atlas et al., "MD-Logic Artificial Pancreas System: A pilot study in adults with type 1 diabetes", Diabetes Care, vol. 33, No. 5, Feb. 11, 2010, pp. 1071-1076.

* cited by examiner

ADAPTATION OF AUTOMATIC INSULIN DELIVERY (AID) FOR USERS WITH BASAL TO BOLUS MISMATCH

RELATED APPLICATIONS

This application claims the benefit of U.S. Provisional Patent Application No. 63/155,555, filed Mar. 2, 2021, the contents of which are incorporated herein by reference in their entirety.

BACKGROUND

Conventional automated insulin delivery (AID) systems work on the assumption that basal insulin constitutes 50% of a user's total daily insulin (TDI) needs. This works well for many users but not as well for many other users. For example, some users may rely heavily on insulin boluses for their daily insulin needs, so the basal insulin amounts such users get from an AID system should be less than 50% of TDI. Other users may eat a low carbohydrate diet and thus, may not use many insulin boluses. For such users, the basal insulin should be set at a level greater than 50% of TDI.

In addition, conventional systems determine TDI for a user according to a standard formula, such as setting the TDI as (the weight of the user divided by 4) units of insulin per day. This standard formula does not provide an accurate estimate of TDI for many users. For such users, their actual TDI is substantially different from the TDI calculated according to the standard formula.

SUMMARY

In accordance with an inventive aspect, an insulin delivery device includes a pump for pumping insulin to a user and a processor for controlling delivery of basal insulin to the user via the pump. The processor is configured for performing the following: establishing an initial current basal amount of insulin to be delivered to the user per a time period of up to a day as a portion of an estimated total daily insulin (TDI) for the user; determining an average actual TDI for the user over a period of days, wherein the average actual TDI for each day in the period of days is a sum of basal insulin and bolus insulin delivered for the day; and updating the current basal amount of insulin to be delivered to the user for the time period from the initial current basal amount to a new basal amount based on the average actual TDI for the user over the period of days.

The time period may be a day, and the initial current basal amount to be delivered to the user for the time period may be established as half of the estimated TDI for the user. The updating of the current basal amount of insulin to be delivered to the user per the time period may comprise updating the current basal amount of insulin to be delivered per the time period to decrease a difference between the initial current basal amount of insulin to be delivered to the user per the time period and a fraction of the average actual TDI for the user over the period of days. How much the difference between the initial current basal amount of insulin to be delivered to the user per the time period and the fraction of the average actual TDI for the user over the period of days is decreased may depend on how many days are in the period of days or on a weighting factor.

The processor may be further configured for: extending the period of days by an additional day; determining an average actual TDI for the user over the extended period of days; and updating the current basal amount of insulin to be delivered for the user per the time period to an updated amount as a fractional value of the average actual TDI for the user over the extended period of days.

The time period may be an hour, and the updating of the current basal amount to be delivered to the user for the time period to a new basal amount may comprise calculating the new basal amount $b_{updated}$ so that $$b_{updated} = S \cdot \frac{TDI_{new}}{24}$$

$$TDI_{new} = (1 - X \cdot N_{days})TDI_{old} + X \cdot N_{days} I_{total}$$

where $N_{days}$ is a number of days in the period of days, $TDI_{old}$ is the estimated TDI for the user, S is a ratio, and $TDI_{new}$ is the average actual TDI for the user over the extended period of days. S may be a constant. S may be a variable with a value based on a historical ratio of basal amounts delivered for a day to TDI for the user. X is a parameter defining the weighting the new insulin delivery history will be applied versus the prior TDI setting, and can range from 0 (no adaptivity) to 1 (full trust of the most recent insulin history). This can be typically set to 0.2 for an approximate adaptation to 80% of the new insulin history over 1 week.

The current basal amount may be an amount per hour, and the updating of the current basal amount to be delivered to the user to a new basal amount may comprise calculating the new basal amount $b_{new}$ so that $$b_{new} = S \cdot \frac{TDI_{new}}{24}$$

$$TDI_{new} = (1 - X \cdot N_{days})TDI_{old} + X \cdot N_{days} I_{total}$$

where $N_{days}$ is a number of days in the period of days, $TDI_{old}$ is the estimated TDI for the user, S is a ratio, and $TDI_{new}$ is the average actual TDI for the user over the extended period of days.

S may have a value of $S_{new}$, which is determined as:

$$S_{new} = (1 - X \cdot N_{days})S_{old} + X \cdot N_{days} \frac{I_{basal}}{I_{total}}$$

where $S_{new}$ is a newly calculated value of S, $S_{old}$ is a most recent value for S, $I_{basal}$ is an amount of basal insulin delivered for the period of days and $I_{total}$ is a total amount of insulin delivered to the user for the period of days.

In accordance with another inventive aspect, a method includes, with a processor of an electronic device, establishing an initial current basal amount of insulin to be delivered to the user per a time period of up to a day as a portion of an estimated total daily insulin (TDI) for the user. An average actual TDI for the user over a period of days is determined with the processor of the electronic device. The average actual TDI for each day in the period of days is a sum of basal insulin and bolus insulin delivered for the day. The current basal amount of insulin to be delivered to the user for the time period is updated with the processor from the initial current basal amount to a new basal amount based on the average actual TDI for the user over the period of days.

The electronic device may be an insulin delivery device. The time period may be a day, and the initial current basal amount to be delivered to the user for the time period may be established as half of the estimated TDI for the user. The updating of the current basal amount of insulin to be delivered to the user per the time period may comprise updating the current basal amount of insulin to be delivered per the time period to decrease a difference between the initial current basal amount of insulin to be delivered to the user per the time period and a fraction of the average actual TDI for the user over the period of days. How much the difference between the initial current basal amount of insulin to be delivered to the user per the time period and the fraction of the average actual TDI for the user over the period of days is decreased may depend on how many days are in the period of days and/or a weighting factor.

The method may further include extending the period of days by an additional day; determining an average actual TDI for the user over the extended period of days; and updating the current basal amount of insulin to be delivered for the user per the time period to an updated amount as a fractional value of the average actual TDI for the user over the extended period of days.

The time period may be an hour, and the updating of the current basal amount to be delivered to the user for the time period to a new basal amount may comprise calculating the new basal amount $b_{updated}$ so that $$b_{updated} = S_{new} \cdot \frac{TDI_{new}}{24}$$

$$TDI_{new} = (1 - X \cdot N_{days})TDI_{old} + X \cdot N_{days} I_{total}$$

where $N_{days}$ is a number of days in the period of days, $TDI_{old}$ is the estimated TDI for the user, S is a ratio, and $TDI_{new}$ is the average actual TDI for the user over the extended period of days.

In accordance with an additional inventive aspect, an insulin delivery device, includes a pump for pumping insulin to a user and a processor for controlling delivery of basal insulin to the user via the pump. The processor is configured for performing the following: establishing a current basal amount of insulin to be delivered to the user per hour; determining an average actual TDI for the user over a period of days, wherein the average actual TDI for each day in the period of days is a sum of basal insulin and bolus insulin delivered for the day; determining a new value of a desired ratio of basal insulin per hour to an hourly portion of total daily insulin, designated as $S_{new}$, as follows:

$$S_{new} = (1 - X \cdot N_{days})S_{old} + X \cdot N_{days} \cdot \frac{\left(\frac{I_{basal}}{I_{total}} + 0.5\right)}{2}$$

where $N_{days}$ is a number of days in the period of days, $S_{old}$ is most recent value of a desired ratio of basal insulin per hour to an hourly portion of total daily insulin, $I_{basal}$ is an amount of basal insulin delivered for the period of days and $I_{total}$ is a total amount of insulin delivered to the user for the period of days; and updating the current basal amount of insulin to be delivered to the user for the time period from the initial current basal amount to a new basal amount $b_{new}$ as:

$$b_{updated} = S_{new} \cdot \frac{TDI_{new}}{24}$$

$$TDI_{new} = (1 - X \cdot N_{days})TDI_{old} + X \cdot N_{days} I_{total}$$

where $TDI_{new}$ is the average actual TDI for the user over the period of days and $TDI_{old}$ is a most recent estimate or actual TDI value for the user.

DETAILED DESCRIPTION

Exemplary embodiments may provide more customized basal insulin amounts for users to better regulate blood glucose (BG) concentration levels. The exemplary embodiments do not statically assume that the daily basal amount for each user is 50% of TDI. Instead, actual TDI data may be gathered for each user and may be used to adjust the TDI value for that user to an updated value. In addition, the ratio of basal to TDI may be adjusted for the user based on the actual ratio determined from data gathered over one or more days. As a result, better BG concentration level control may be realized.

The degree of adaptivity of the basal insulin amount per a time period, like per day or per hour, may be based on how much historical data is available. More extensive historical data being available may result in greater adaptivity of the TDI, greater adaptivity of the ratio of basal insulin amount to TDI and ultimately greater adaptivity in the basal amount. The degree of adaptivity also may be limited to a maximum amount relative to the ideal 50% amount relative to TDI in some exemplary embodiments. This helps to ensure that the adaptation does not result in a ratio that is undesirable for a user.

Figure 1:
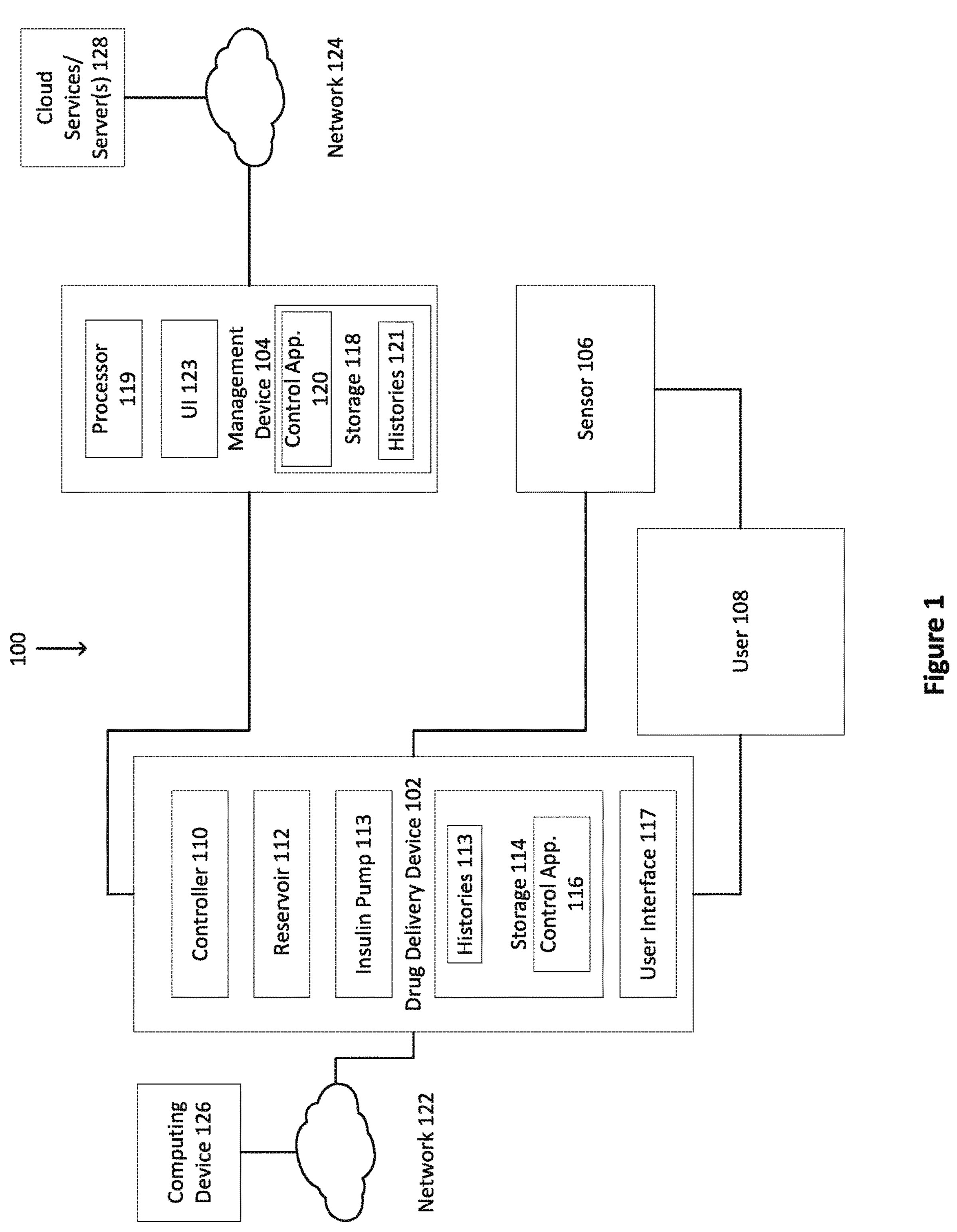
FIG. 1 depicts an illustrative drug delivery system suitable for an exemplary embodiment.

FIG. 1 depicts an illustrative drug delivery system (100) that is suitable for delivering insulin to a user (108) in an exemplary embodiment. The drug delivery system (100) includes a drug delivery device (102). The drug delivery device may deliver a variety of different drugs, including insulin, glucagon, GLP-1, pain management agents, therapeutic agents, chemotherapy agents, hormonal agents, a combination thereof, and the like. That said, the methods described below focus on the delivery of insulin but could equally apply to other drugs or a combination of insulin and another drug, such as GLP-1. The drug delivery device (102) may be a wearable device that is worn on the body of the user (108). The drug delivery device (102) may be directly coupled to a user (e.g., directly attached to a body part and/or skin of the user (108) via an adhesive or the like). In an example, a surface of the drug delivery device (102) may include an adhesive to facilitate attachment to the user (108).

The drug delivery device (102) may include a controller (110). The controller (110) may be implemented in hardware, software, or any combination thereof. The controller (110) may, for example, be a microprocessor, a logic circuit, a field programmable gate array (FPGA), an application specific integrated circuit (ASIC) or a microcontroller coupled to a memory. The controller (110) may maintain a date and time as well as other functions (e.g., calculations or the like). The controller (110) may be operable to execute a control application (116) stored in the storage (114) that enables the controller (110) to direct operation of the drug delivery device (102). The storage (114) may hold histories (113) for a user, such as a history of automated insulin deliveries, a history of bolus insulin deliveries, meal event history, exercise event history and the like. In addition, the controller (110) may be operable to receive data or information. The storage (114) may include both primary memory and secondary memory. The storage may include random access memory (RAM), read only memory (ROM), optical storage, magnetic storage, removable storage media, solid state storage or the like.

The drug delivery device (102) may include a reservoir (112) for storing one or more drugs, such as insulin, for delivery to the user (108) as warranted. A fluid path to the user (108) may be provided, and the drug delivery device (102) may expel the drug from the reservoir (112) to deliver the drug to the user (108) via the fluid path. The fluid path may, for example, include tubing coupling the drug delivery device (102) to the user (108) (e.g., tubing coupling a cannula to the reservoir (112)).

There may be one or more communications links with one or more devices physically separated from the drug delivery device (102) including, for example, a management device (104) of the user and/or a caregiver of the user and/or a sensor (106) for sensing an analyte, such as BG level concentration. The communication links may include any wired or wireless communication link operating according to any known communications protocol or standard, such as Bluetooth®, Wi-Fi, a near-field communication standard, a cellular standard, or any other wireless protocol The drug delivery device (102) may also include a user interface (117), such as an integrated display device for displaying information to the user (108) and in some embodiments, receiving information from the user (108). The user interface (117) may include a touchscreen and/or one or more input devices, such as buttons, knob or a keyboard.

The drug delivery device (102) may interface with a network (122). The network (122) may include a local area network (LAN), a wide area network (WAN) or a combination therein. A computing device (126) may be interfaced with the network, and the computing device may communicate with the drug delivery device (102).

The sensor (106) may be coupled to the user (108) by, for example, adhesive or the like and may provide information or data on one or more medical conditions and/or physical attributes of the user (108). The sensor (106) may, in some exemplary embodiments provide periodic BG concentration measurements and may be a continuous glucose monitor (CGM), or another type of device or sensor that provides BG measurements. The sensor (106) may be physically separate from the drug delivery device (102) or may be an integrated component thereof. The sensor (106) may provide the controller (110) with data indicative of measured or detected BG levels of the user (108). The information or data provided by the sensor (106) may be used to adjust drug delivery operations of the drug delivery device (102).

The drug delivery system (100) may also include the management device (104). In some embodiments, there is no need for a management device (104); rather the drug delivery device (102) includes the functionality provided by the management device (104) such that the drug delivery device (102) can program or adjust operation of the drug delivery device (102) and/or the sensor (104) without input from a remote management device (104). The management device (104) may be a special purpose device, such as a dedicated personal diabetes manager (PDM) device. The management device (104) may be a programmed general-purpose device, such as any portable electronic device including, for example, a dedicated controller, such as processor, a microcontroller or the like. The management device (104) may be used to program or adjust operation of the drug delivery device (102) and/or the sensor (104). The management device (104) may be any portable electronic device including, for example, a dedicated device, a smartphone, a smartwatch or a tablet. In the depicted example, the management device (104) may include a processor (119) and a storage (118). The processor (119) may execute processes to manage a user's BG levels and for control the delivery of the drug or therapeutic agent to the user (108). The processor (119) may also be operable to execute programming code stored in the storage (118). For example, the storage may be operable to store one or more control applications (120) for execution by the processor (119). The storage (118) may store the control application (120), histories (121) like those described above for the drug delivery device (102) and other data and/or programs.

The management device (104) may include a user interface (123) for communicating with the user (108). The user interface may include a display, such as a touchscreen, for displaying information. The touchscreen may also be used to receive input when it is a touch screen. The user interface (UI) (123) may also include input elements, such as a keyboard, buttons, knobs or the like.

The management device (104) may interface with a network (124), such as a LAN or WAN or combination of such networks. The management device (104) may communicate over network (124) with one or more servers or cloud services (128). The role that the one or more servers or cloud services (128) may play in the exemplary embodiments will be described in more detail below.

Figure 2:
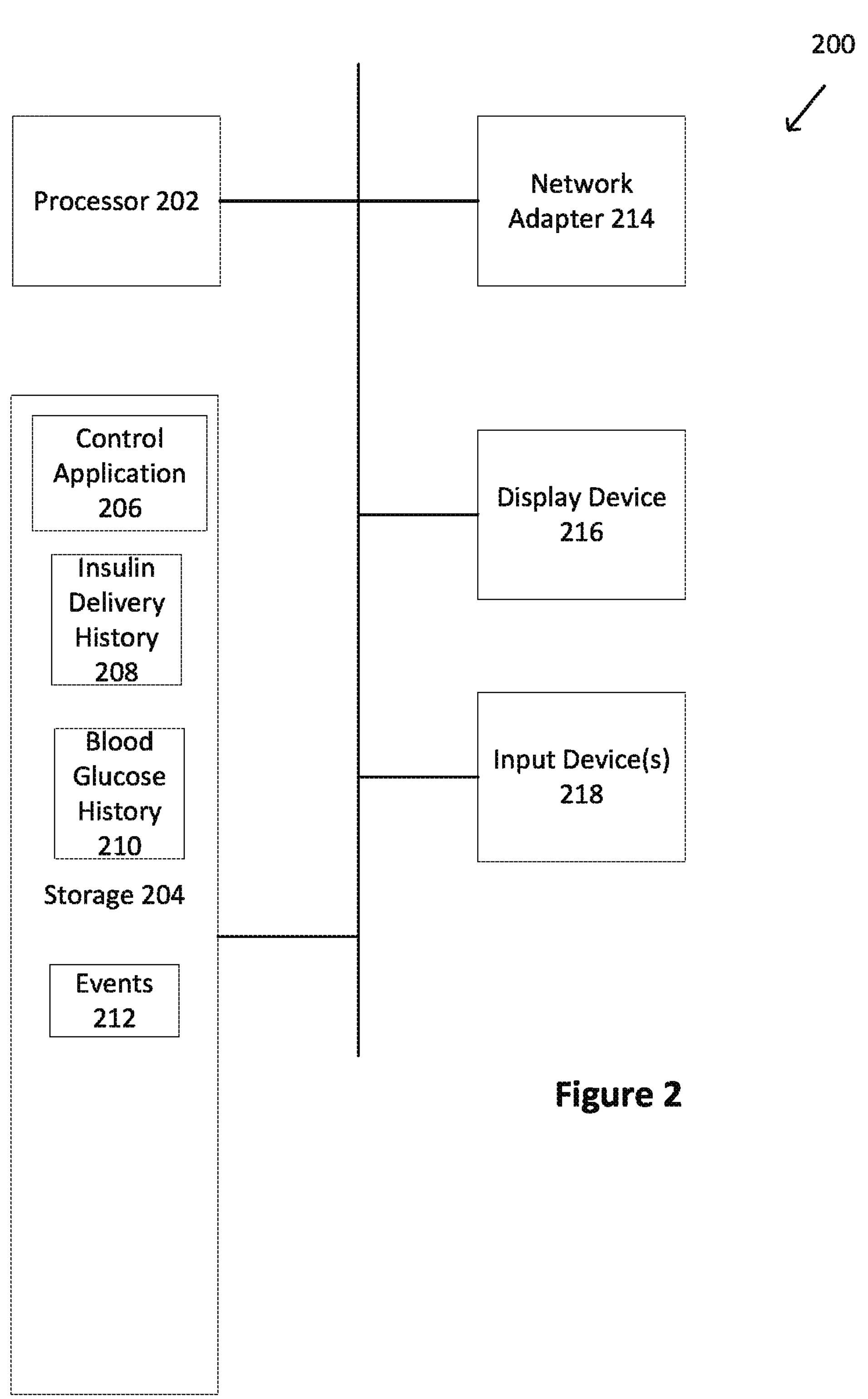
FIG. 2 depicts a block diagram of an illustrative computing device of an exemplary embodiment.

FIG. 2 depicts a block diagram of a device (200) suitable for performing the methods that will be described in more detail below. The device (200) may in different exemplary embodiments be the drug delivery device (102), the management device (104), the computing device (126) or the one or more servers (128). Where the device is the computing device (126), or the one or more servers (128), the device (200) may act in cooperation with the management device (104) and the drug delivery device (102) to perform the methods. The device (200) includes a processor (202) for executing programming instructions. The processor (202) has access to a storage (204). The storage (204) may store an application (206) for performing the methods. This application (206) may be executed by the processor (202). The storage (204) may store an insulin delivery history (208) for the user. The insulin delivery history (208) may contain data regarding the amount of insulin delivered as well as the date and time of the deliveries. The insulin delivery history (208) may also identify if each delivery is a basal delivery or a bolus delivery. The storage (204) may store the BG history (210). The BG history (210) may include BG concentration readings as well as the date and time of such readings. These values may be obtained by the sensor (106). The storage (204) additionally may store information regarding events (212), like meal events and exercise events. The storage may hold information regarding the fuzzy sets (213), including their associated member functions.

The device (200) may include a network adapter (214) for interfacing with networks, like networks (122 and 124). The device (200) may have a display device (216) for displaying video information. The display device (216) may be, for instance, a liquid crystal display (LCD) device, a light emitting diode (LED) device, etc. The device (200) may include one or more input devices (218) for enabling input to be received. Examples of input devices include keyboard, mice, thumb pads, touchscreens, microphones and the like.

In the exemplary embodiments, the controller (110) of the drug delivery device (102) or the processor (119) of the management device (104) running the control application (120) may be responsible for setting what the basal amount of insulin per time period (e.g., per day, per hour, per 5 minutes) is. As was mentioned above, the exemplary embodiments may adapt the basal insulin amount based on historical TDI data. In addition, the exemplary embodiments may adapt the basal insulin amount based on historical data of the ratio of basal insulin to TDI for the user.

Figure 3:
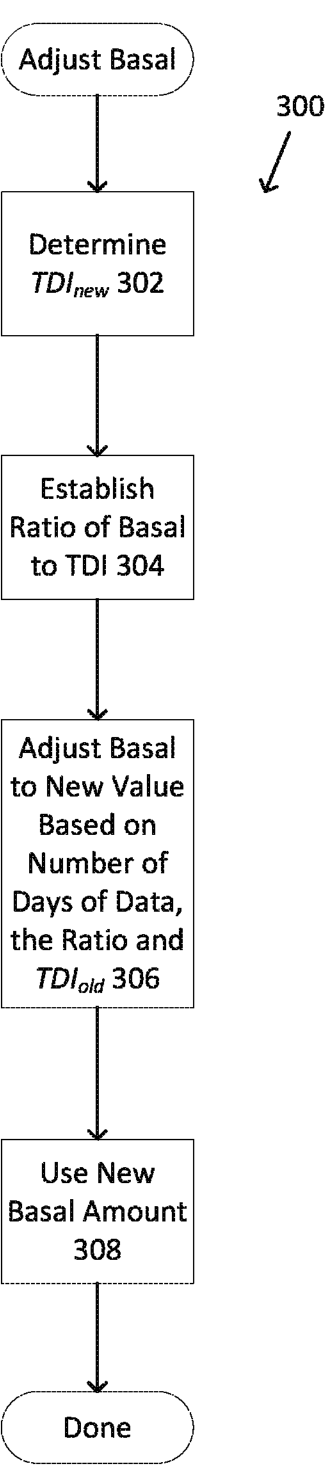
FIG. 3 depicts a flowchart of illustrative steps that may be performed by an exemplary embodiment to adjust the basal amount for a user.

FIG. 3 depicts a flowchart (300) of illustrative steps that may be performed by exemplary embodiments to adjust the basal amount for a user. The basal amount may be for an hour, a day or even a fifteen minute period of time. For illustrative purposes herein, the discussion will relate to an example where the basal amount is for an hour and represents the amount of basal insulin to be delivered to the user over an hour by the drug delivery device (102) under the control of an AID system. Actual TDI data for the user is gathered for a period of days. The TDI is the sum of the basal insulin and bolus insulin delivered to the user for a day (i.e., a 24 hour period). Based on the gathered data a new TDI value, designated as $TDI_{new}$, is determined.

Figure 4:
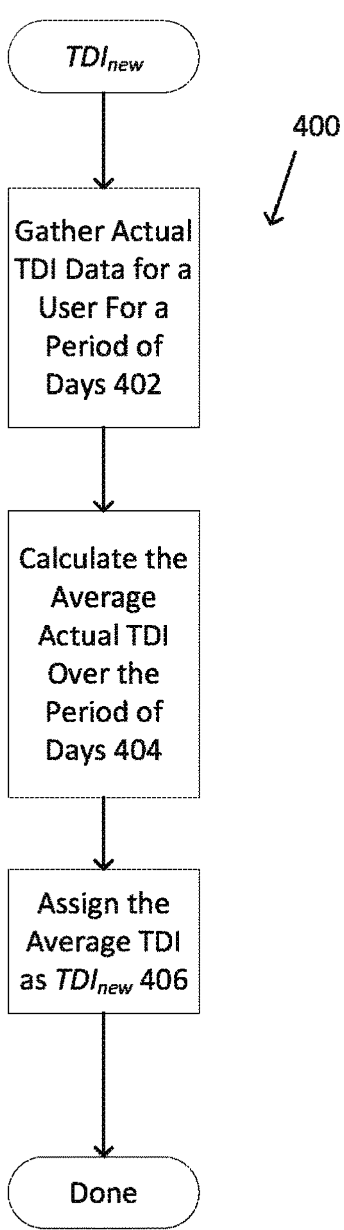
FIG. 4 depicts a flowchart of illustrative steps that may be performed to calculate $TDI_{new}$ in an exemplary embodiment.

FIG. 4 depicts a flowchart (400) of illustrative steps that may be performed to calculate $TDI_{new}$. As was mentioned above actual TDI data is gathered for the user for the period of days (402). The aim of gathering this data is to adjust the TDI value to more accurately reflect the user's actual TDI and to use the actual TDI in determining the basal amount. The period of days may range, for example from 1 to 3 days, preferably the most recent days. An average TDI is determined from the gathered actual TDI data (404). The average may be calculated by summing the TDI values over the period of days and then dividing the sum by the number of days in the period of days. Alternatively, a median value for the TDI may be used in some exemplary embodiments. The average TDI may be designated as $TDI_{new}$ (406).

As shown in FIG. 3, a ratio of basal amount for a day to TDI is established (304). This ratio conventionally has been fixed at ½, such that the basal amount of insulin delivered to the user for a day is 50% of the TDI. The exemplary embodiments accommodate a constant value choice like 50% or accommodate variable values that may change over time. In some exemplary embodiments, actual historical data for the user is used to choose the ratio that is seen with the historical data. The aim is to more accurately select the ratio for the user based on what the ratio has been historically.

Figure 5:
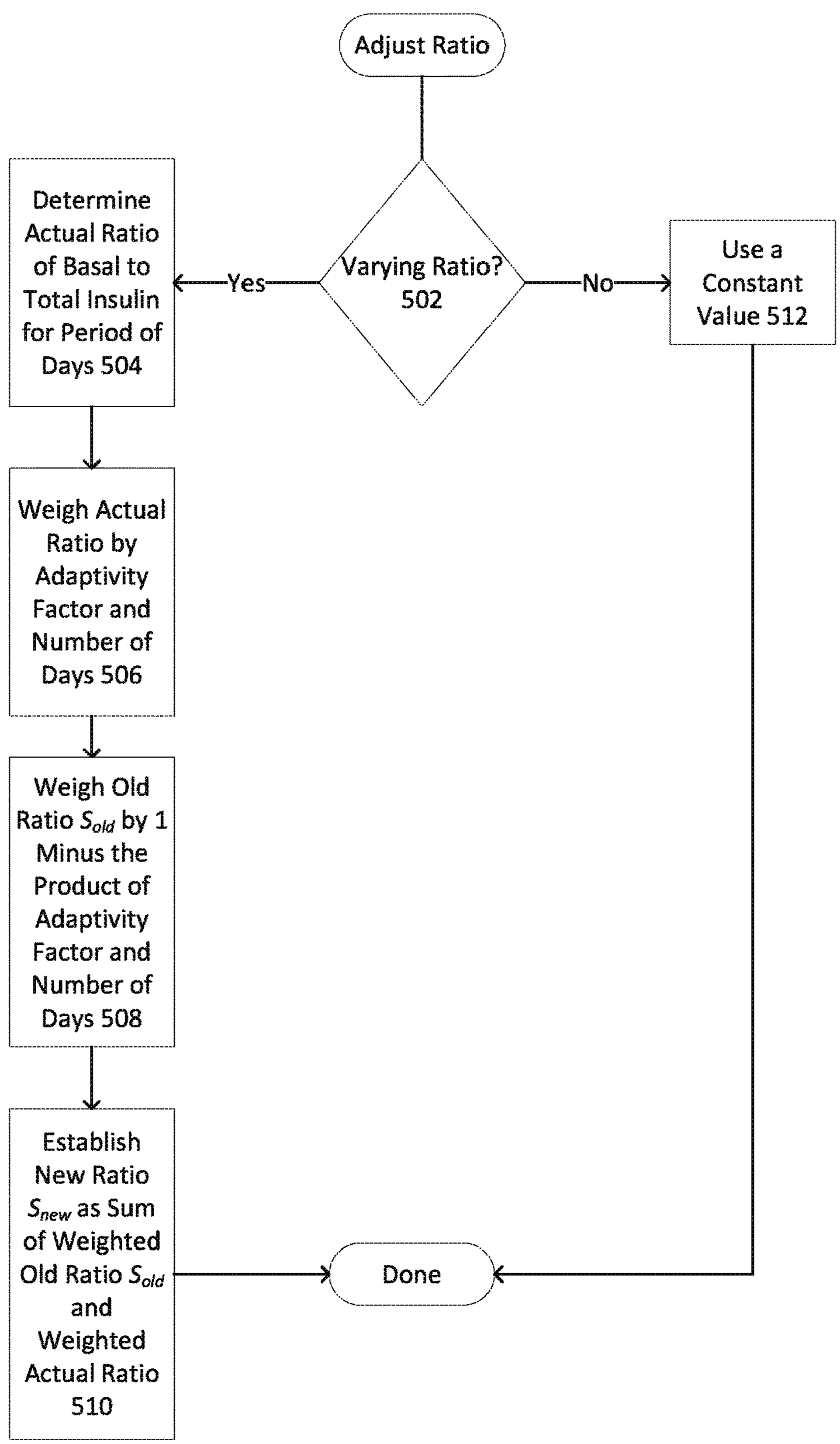
FIG. 5 depicts a flowchart of illustrative steps that may be performed to select the ratio in an exemplary embodiment.

FIG. 5 depicts a flowchart (500) of illustrative steps that may be performed to select the ratio in exemplary embodiments. A decision is made as to whether to have a varying ratio or not (502). This decision may be based on an assessment of whether a non-varying ratio will work well or not for a user. If a varying ratio is desired, data is gathered for a period of days, such as one to three days. The total basal insulin and the total insulin delivered over the period of days are determined, and a ratio of the total basal insulin to total insulin over the period of days is determined (504). This ratio constitutes the actual ratio for the user over the period of days. Generally, the goal is to not switch the ratio immediately to the actual ratio from an old ratio. Instead, it is more desirable to more slowly adapt the ratio. The confidence in the actual ratio is greater with data for more days. As such, the actual ratio is weighed by a product of the number of days and the adaptivity factor (506). Thus, a ratio based on three days of data is more heavily weighed than a ratio based on one day of data. The old ratio, designated as $S_{old}$, is weighed by 1−(adaptivity factor*number of days in the period of days) (508). The new ratio $S_{new}$ is established as the sum of the weighted old ratio $S_{old}$ and the weighted actual ratio.

This formulation of $S_{new}$ may be expressed as:

$$S_{new} = (1 - X \cdot N_{days})S_{old} + X \cdot N_{days}\frac{I_{basal}}{I_{total}}$$

where $N_{days}$ is the number of days in the period of days; $I_{basal}$ is the total basal insulin delivered over the period of days; and $I_{total}$ is the total basal insulin delivered over the period of days. X is the adaptivity factor, controlling how much the adaptivity will weigh the recent insulin delivery history versus the previous settings, and can range from 0 (no adaptivity) to 1 (full trust of the recent history). A nominal value of this parameter is 0.2.

As shown in FIG. 3, once the ratio of basal to TDI is determined, the basal amount may be adjusted to a new value based on the number of days of data, the ratio of basal to TDI and the previous TDI value, $TDI_{old}$ (306). The new basal amount is then used in delivering basal insulin to the user by the insulin delivery device.

One formulation of the new basal amount (designated as $b_{new}$) is:

$$b_{new} = S \cdot \frac{TDI_{new}}{24}$$

$$TDI_{new} = (1 - X \cdot N_{days})TDI_{old} + X \cdot N_{days}I_{total}$$

Figure 6:
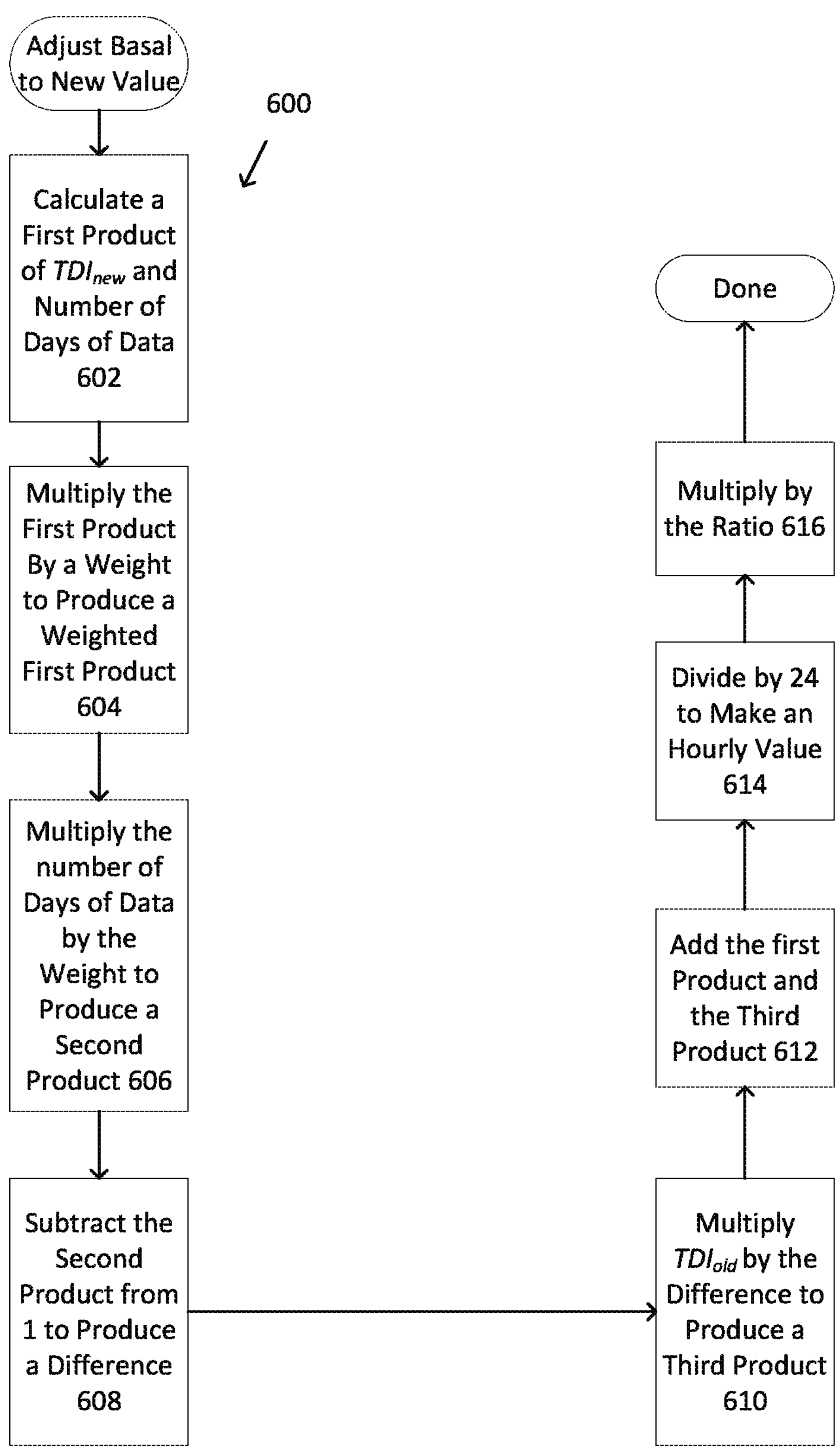
FIG. 6 depicts a flowchart of illustrative steps that may be performed to calculate $b_{new}$ in an exemplary embodiment.

FIG. 6 depicts a flowchart (600) of illustrative steps that may be performed to calculate $b_{new}$. A first product of $TDI_{new}$ and the number of days in the period of days is calculated (i.e., $N_{days}TDI_{new}$) (602). The first product may be multiplied by a weight to produce a weighted first product (604). The weight may be the product of the number of days $N_{days}$ and an adaptivity factor of X. Thus, $TDI_{new}$ has a greater influence on $b_{new}$ the more days of data there is to rely upon. The adaptivity factor helps to ensure that there is a more gradual influence of $TDI_{new}$ on $b_{new}$. The weight of $TDI_{old}$ is based on 1 minus the product of the adaptivity factor (0.2) and $N_{days}$. Thus, the product of $X \cdot N_{days}$ is calculated (606), and that product is subtracted from 1 to produce a difference (608). Then $TDI_{old}$ is multiplied by the difference to produce a third product (610). The third product is added with the weighted $TDI_{new}$ value (612). The resulting sum is divided by 24 to make the value an hourly value rather than a daily value (614). Lastly, the hourly value is multiplied by the ratio $S_{new}$ (616).

This formulation is intended to be illustrative and not limiting. Other formulations may be used, such as with different ratio values and different adaptivity factors. These alternative formulations may rely upon actual historical data for the user and use the historical data to adapt the basal amount for the user.

It may be desirable to limit the degree of adaptivity permitted for the ratio S of basal to TDI. It may not be desirable for the ratio to run too far afield from the more idealized ratio of 50%. A user may be better suited by maintaining the ratio S within an acceptable range of S. For example, perhaps a user may be relying on boluses too much, and it would be healthier for them to not rely on the boluses so much. More generally, the user's pattern of insulin delivery may be not very ideal and the limits on adaptivity help to constrain such a pattern.

Figure 7:
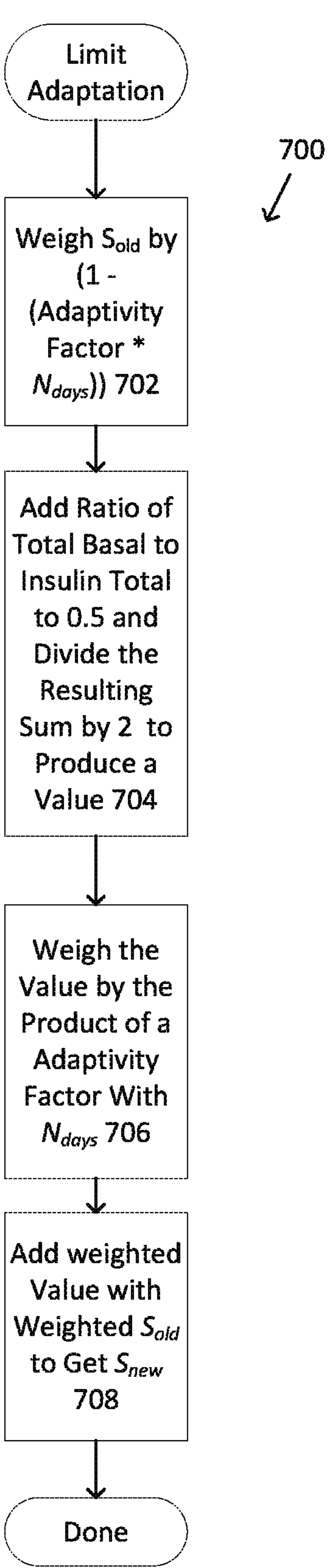
FIG. 7 depicts a flowchart of illustrative steps for limiting the adaptation of $S_{new}$ relative to a benchmark in an exemplary embodiment.

FIG. 7 shows a flowchart (700) of illustrative steps that may be performed to limit the degree of adaptivity for S. The flowchart sets forth steps that may be performed to calculate $S_{new}$ with such limits according to the following formulation:

$$S_{new} = (1 - X \cdot N_{days})S_{old} + X \cdot N_{days} \cdot \frac{\left(\frac{I_{basal}}{I_{total}} + 0.5\right)}{2}$$

The old ratio $S_{old}$ is weighted by the difference between 1 and the product of the number of days in the period of days ($N_{days}$) with the adaptivity factor (X). This weighting is the same as the formulation of $S_{new}$ that was set forth previously (702). Where the formulation differs is in how the gathered data of $I_{basal}$ and $I_{total}$ are used in the formulation. Instead of just using the ratio of $$\frac{I_{basal}}{I_{total}},$$

and weighting that ratio. The new formulation adds the ratio $$\frac{I_{basal}}{I_{total}}$$

to 0.5 and then divides by 2 (704). The practical effect of this is to average $$\frac{I_{basal}}{I_{total}}$$

and 0.5. The resulting value is weighted by the product of the adaptivity factor (X) and $N_{days}$ (706). The resulting weighted value is summed with the weighted value of $S_{old}$ to get a value for $S_{new}$ (708).

The practical effect of the change in the formulation is to limit the weighted value. When only $$\frac{I_{basal}}{I_{total}}$$

is used, the range of possible values extends from 0 to 1, whereas when $$\frac{\left(\frac{I_{basal}}{I_{total}} + 0.5\right)}{2}$$

is used, the range of possible values extends from 0.25 to 0.75. Hence, the contribution of the actual data regarding insulin is more range bound closer to 0.5.

Figure 8A:
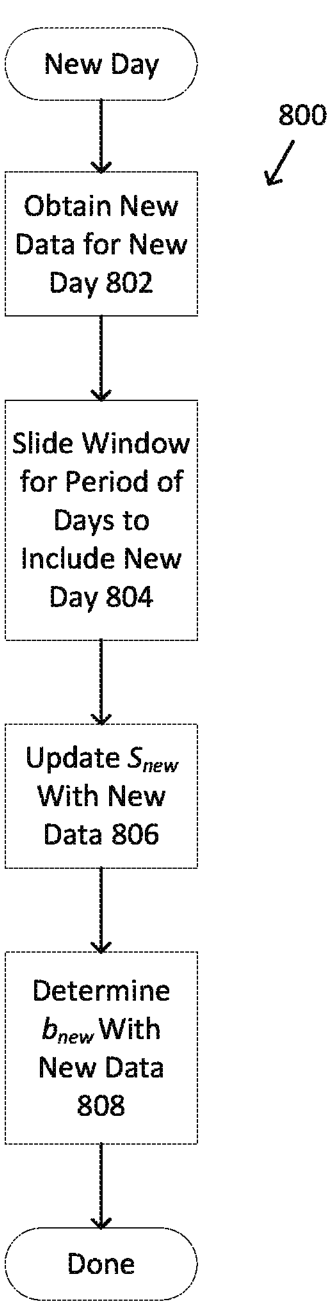
FIG. 8A depicts a flowchart of illustrative steps that may be performed to update the $b_{new}$ value on an ongoing daily basis in an exemplary embodiment.
Figure 8B:
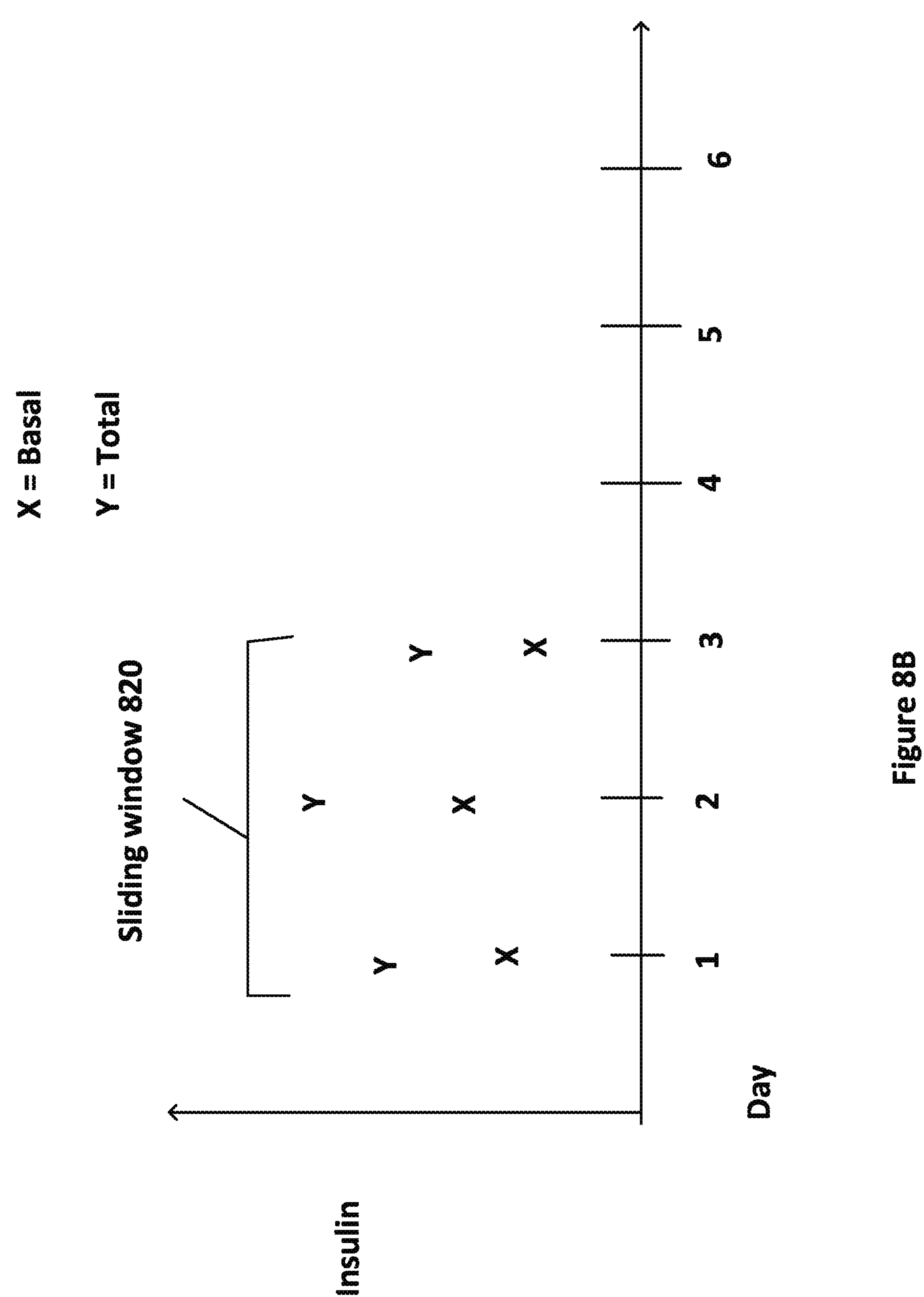
FIGS. 8B and 8C illustrate an example of a sliding data window for updating the $b_{new}$ value on an ongoing daily basis in an exemplary embodiment.
Figure 8C:
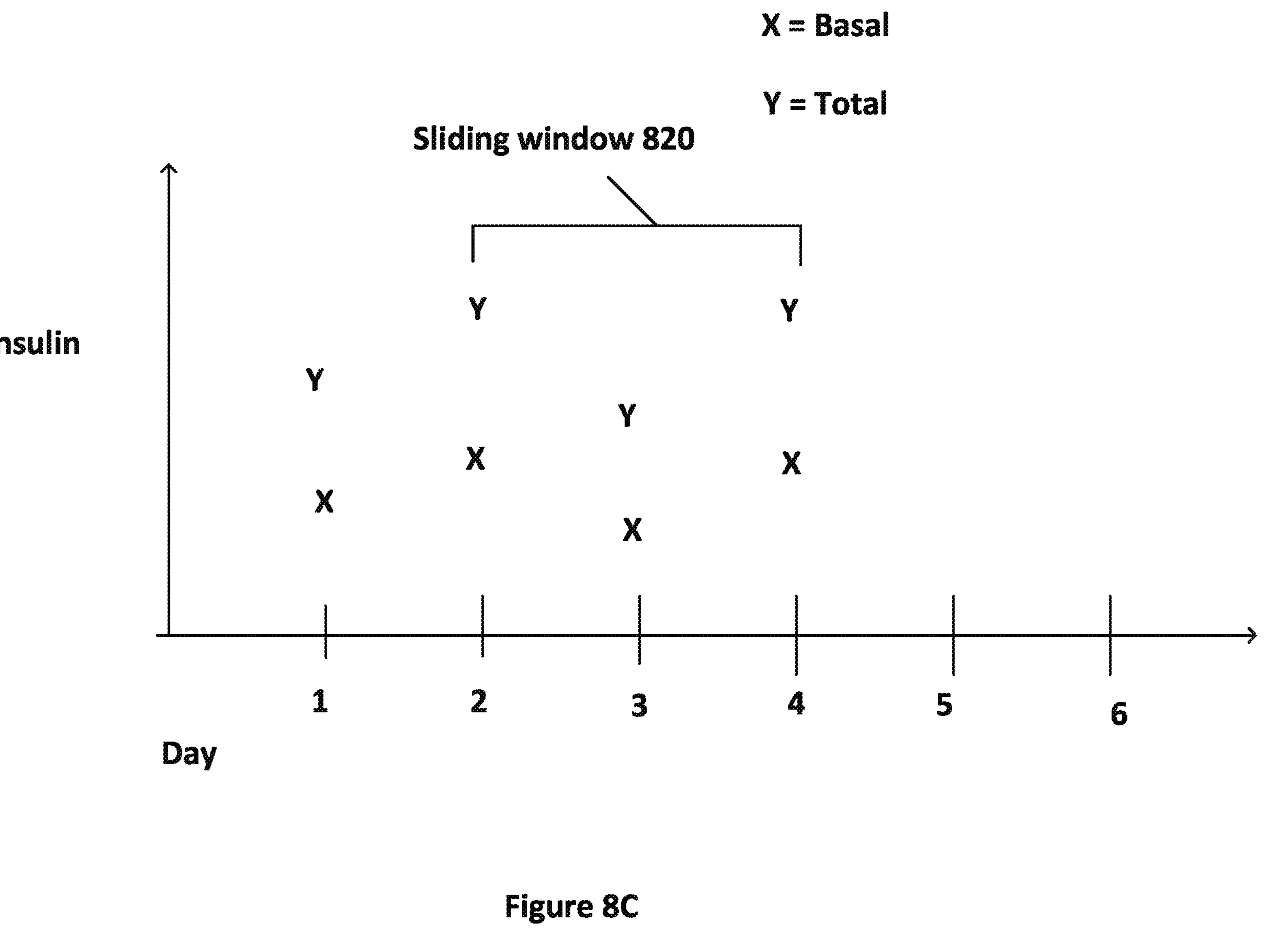

The basal amount $b_{new}$ may be updated on an ongoing basis, such as on a daily basis. FIG. 8A depicts a flowchart (800) of illustrative steps that may be performed to realize the updating. The insulin data for a new data is obtained (802). This may include basal insulin for the day and total insulin for the day (e.g., TDI or $I_{total}$). The period of days is shifted forward a day to include the new day (804). This may be viewed as shifting a sliding window forward by a day. FIG. 8B shows insulin data (basal and total) for days 1, 2 and 3. The period of days includes days 1, 2 and 3 as indicated by the sliding window 820. After day 4 data is obtained, the sliding window 820 for the period of days may be shifted forward a day as indicated in FIG. 8C. The ratio $S_{new}$ may be updated based on the new data in the period of days (if the ratio is not fixed) using one of the formulations set forth above (806). The new value of $b_{new}$ may then be determined using the updated data for the period of days, such as by using the formulation set forth above (808).

While exemplary embodiments have been described herein. Various changes in form and detail relative to the exemplary embodiments without departing from the intended inventive scope as defined in the appended claims.

The invention claimed is:

1. An insulin delivery device, comprising:

a pump for pumping insulin to a user;

a processor for controlling delivery of basal insulin to the user via the pump, the processor configured for performing the following:

establishing an initial current basal amount of insulin to be delivered to the user per a time period of up to a day as a portion of an estimated total daily insulin (TDI) for the user;

determining an average of actual TDIs for the user over a period of days, wherein the actual TDI for each day in the period of days is a sum of basal insulin and bolus insulin delivered for the day;

determining a new TDI value from the average of the actual TDIs for the user over the period of days;

determining a ratio of basal insulin delivered to the user over the period of days relative to the actual TDIs of the user for the days of the period of days; and adapting the initial current basal amount of insulin to be delivered to the user for the time period to a new basal amount based on a product of the ratio and the new TDI value for the user.

2. The insulin delivery device of claim 1, wherein the time period is a day and wherein the initial current basal amount to be delivered to the user for the time period is established as half of the estimated TDI for the user.

3. The insulin delivery device of claim 1, wherein the adapting the initial current basal amount of insulin to be delivered to the user per the time period comprises updating the new basal amount of insulin to be delivered per the time period to decrease a difference between the initial current basal amount of insulin to be delivered to the user per the time period and a fraction of the average actual TDI for the user over the period of days.

4. The insulin delivery device of claim 3, wherein how much the difference between the initial current basal amount of insulin to be delivered to the user per the time period and the fraction of the average actual TDI for the user over the period of days is decreased depends on how many days are in the period of days.

5. The insulin delivery system of claim 3, wherein how much the difference between the initial current basal amount of insulin to be delivered to the user per the time period and the fraction of the average actual TDI for the user over the period of days is decreased depends on a weighting factor.

6. The insulin delivery system of claim 1, wherein the processor is further configured for performing:

extending the period of days by an additional day;

determining an average actual TDI for the user over the extended period of days; and updating the adapted current basal amount of insulin to be delivered for the user per the time period to an updated amount as a fractional value of the average actual TDI for the user over the extended period of days.

7. The insulin delivery system of claim 6, wherein the time period is an hour and wherein the updating of the adapted current basal amount to be delivered to the user for the time period to a new basal amount comprises calculating the new basal amount $b_{updated}$ as $$b_{updated} = S \cdot \frac{TDI_{new}}{24}$$

$$TDI_{new} = (1 - X \cdot N_{days})TDI_{old} + X \cdot N_{days} I_{total}$$

where $N_{days}$ is a number of days in the period of days, $TDI_{old}$ is the estimated TDI for the user, S is the ratio, and $TDI_{new}$ is the determined new TDI value, X is an adaptivity factor that can range from 0 to 1.

8. The insulin delivery system of claim 7, wherein S is a constant.

9. The insulin delivery system of claim 7, wherein S is a variable with a value based on the ratio.

10. The insulin delivery system of claim 1, wherein the current basal amount is an amount per hour and wherein the adapting of the current basal amount to be delivered to the user to a new basal amount comprises calculating the new basal amount $b_{new}$ as $$b_{new} = S \cdot \frac{TDI_{new}}{24}$$

$$TDI_{new} = (1 - X \cdot N_{days})TDI_{old} + X \cdot N_{days} I_{total}$$

where $N_{days}$ is a number of days in the period of days, $TDI_{old}$ is the estimated TDI for the user, S is the ratio, and $TDI_{new}$ is the new TDI value.

11. The insulin delivery system of claim 10, wherein S has a value of $S_{new}$, which is determined as:

$$S_{new} = (1 - X \cdot N_{days})S_{old} + X \cdot N_{days} \frac{I_{basal}}{I_{total}}$$

where $S_{new}$ is a newly calculated value of S, $S_{old}$ is a most recent value for S, $I_{basal}$ is an amount of basal insulin delivered for the period of days and $I_{total}$ is a total amount of insulin delivered to the user for the period of days.

12. A method, comprising:

with a processor of an electronic device, establishing an initial current basal amount of insulin to be delivered to the user per a time period of up to a day as a portion of an estimated total daily insulin (TDI) for the user;

with the processor of the electronic device, determining an average actual TDI for the user over a period of days, wherein the average actual TDI for each day in the period of days is a sum of basal insulin and bolus insulin delivered for the day;

with the processor of the electronic device, determining a new TDI value from the average of the actual TDIs for the user over the period of days;

with the processor of the electronic device, determining a ratio of basal insulin delivered to the user over the period of days relative to the actual TDIs of the user for the days of the period of days; and with the processor of the electronic device, adapting the initial current basal amount of insulin to be delivered to the user for the time period to a new basal amount based on a product of the ratio and the new TDI value for the user.

13. The method of claim 12, wherein the electronic device is an insulin delivery device.

14. The method of claim 12, wherein the time period is a day and wherein the initial current basal amount to be delivered to the user for the time period is established as half of the estimated TDI for the user.

15. The method of claim 12, wherein the adapting the initial current basal amount of insulin to be delivered to the user per the time period comprises decreasing a difference between the initial current basal amount of insulin to be delivered to the user per the time period and a fraction of the average actual TDI for the user over the period of days.

16. The method of claim 15, wherein how much the difference between the initial current basal amount of insulin to be delivered to the user per the time period and the fraction of the average actual TDI for the user over the period of days is decreased depends on how many days are in the period of days.

17. The method of claim 15, wherein how much the difference between the initial current basal amount of insulin to be delivered to the user per the time period and the fraction of the average actual TDI for the user over the period of days is decreased depends on a weighting factor.

18. The method of claim 12, further comprising:

extending the period of days by an additional day;

determining an average actual TDI for the user over the extended period of days; and updating the adapted current basal amount of insulin to be delivered for the user per the time period to an updated amount as a fractional value of the average actual TDI for the user over the extended period of days.

19. The method of claim 18, wherein the time period is an hour and wherein the updating of the adapted current basal amount to be delivered to the user for the time period to a new basal amount comprises calculating the new basal amount $b_{updated}$ as $$b_{updated} = S \cdot \frac{TDI_{new}}{24}$$

$$TDI_{new} = (1 - X \cdot N_{days})TDI_{old} + X \cdot N_{days} I_{total}$$

where $N_{days}$ is a number of days in the period of days, $TDI_{old}$ is the estimated TDI for the user, S is the ratio, and $TDI_{new}$ is the new TDI value.

20. An insulin delivery device, comprising:

a pump for pumping insulin to a user;

a processor for controlling delivery of basal insulin to the user via the pump, the processor configured for performing the following:

establishing a current basal amount of insulin to be delivered to the user per hour;

determining an average actual TDI for the user over a period of days, wherein the average actual TDI for each day in the period of days is a sum of basal insulin and bolus insulin delivered for the day;

determining a new value of a desired ratio of basal insulin per hour to an hourly portion of total daily insulin, designated as $S_{new}$, as:

$$S_{new} = (1 - X \cdot N_{days})S_{old} + X \cdot N_{days} \cdot \frac{\left(\frac{I_{basal}}{I_{total}} + 0.5\right)}{2}$$

where $N_{days}$ is a number of days in the period of days, $S_{old}$ is most recent value of a desired ratio of basal insulin per hour to an hourly portion of total daily insulin, $I_{basal}$ is an amount of basal insulin delivered for the period of days and $I_{total}$ is a total amount of insulin delivered to the user for the period of days; and adapting the current basal amount of insulin to be delivered to the user for the time period from the initial current basal amount to a new basal amount $b_{new}$ as:

$$b_{new} = S \cdot \frac{TDI_{new}}{24}$$

$$TDI_{new} = (1 - X \cdot N_{days})TDI_{old} + X \cdot N_{days} I_{total}$$

where Sis $S_{new}$ and $TDI_{old}$ a is a most recent estimate or actual TDI value for the user.

* * * * *